US011017880B2

(12) United States Patent
Deshpande et al.

(10) Patent No.: US 11,017,880 B2
(45) Date of Patent: May 25, 2021

(54) SCREENING OF LARGE-SCALE GENETIC INTERACTION NETWORKS

(71) Applicant: Regents of the University of Minnesota, Minneapolis, MN (US)

(72) Inventors: Raamesh Deshpande, Fremont, CA (US); Justin Nelson, St Paul, MN (US); Chad L. Myers, Arden Hills, MN (US); Scott William Simpkins, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 846 days.

(21) Appl. No.: 15/475,347

(22) Filed: Mar. 31, 2017

(65) Prior Publication Data

US 2017/0286595 A1 Oct. 5, 2017

Related U.S. Application Data

(60) Provisional application No. 62/317,038, filed on Apr. 1, 2016.

(51) Int. Cl.
*G16B 20/00* (2019.01)
*G16B 30/00* (2019.01)
*G16C 20/60* (2019.01)
*G16B 35/00* (2019.01)

(52) U.S. Cl.
CPC .............. *G16B 20/00* (2019.02); *G16B 30/00* (2019.02); *G16B 35/00* (2019.02); *G16C 20/60* (2019.02)

(58) Field of Classification Search
None
See application file for complete search history.

(56) References Cited

U.S. PATENT DOCUMENTS

| | | |
|---|---|---|
| 2014/0288846 A1 | 9/2014 | Chance et al. |
| 2016/0032390 A1 | 2/2016 | Hakonarson et al. |
| 2019/0057183 A1 | 2/2019 | Fang et al. |

FOREIGN PATENT DOCUMENTS

| | | |
|---|---|---|
| WO | 2017160842 | 9/2017 |

OTHER PUBLICATIONS

"International Application Serial No. PCT/US2017/022308, International Search Report dated May 31, 2017", 2 pgs.
"International Application Serial No. PCT/US2017/022308, Written Opinion dated May 31, 2017", 7 pgs.
Bellay, Jeremy, et al., "Putting genetic interactions in context through a global modular decomposition", Genome Research, 21(8), (2011), 1375-1387.
Bellay, Jeremy, et al., "Putting genetic interactions in context through a global modular decomposition", Supplemental Materials, Genome Research, 21(8), (2011), 14 pgs.
Beyer, Andreas, et al., "Integrating physical and genetic maps: from genomes to interaction networks", NIH Public Access, Author Manuscript, published in final edited form as:: Nature Reviews Genetics, 8(9), (2007), 699-710, 2007), 26 pgs.
Costanzo, Michael, et al., "The Genetic Landscape of a Cell", Science, New Series, 327(5964), (2010), 425-431.
Deshpande, Raamesh, "Optimizing functional screening strategies for drug target prediction", 2012 Intelligent Systems for Molecular Biology, Long Beach, CA, Jul. 16, 2012, Optimizing functional genomics screening strategies for drug target prediction. 20 minute talk, high-level overview of method and summary of applications in chemical genomics (no technical details of the algorithm), (2012), 21 pgs.
Friedman, Nir, et al., "The DNA Damage Road Map", Science, 330(6009), (2010), 1327-1328.
Krawitz, Peter M., et al., "Identity-by-descent filtering of exome sequence data identifies PIGV mutations in hyperphosphatasia mental retardation syndrome", Nature Genetics, 42(10), (2010), 827-829.
Myers, Chad L., et al., "Finding function: evaluation methods for functional genomic data", BMC Genomics, 7, (2006), 15 pgs.
Parsons, Ainslie B., et al., "Exploring the Mode-of-Action of Bioactive Compounds by Chemical-Genetic Profiling in Yeast". Cell, 126, (2006), 611-625.
Ryan, Colm J., et al., "Hierarchical Modularity and the Evolution of Genetic Interactomes across Species". Mol Cell, 46, (2012), 691-704.
Anastassiou, D., et al., "Computational analysis of the synergy among multiple interacting genes", Molecular Systems Biology, 3: 83, (2007), 1-8.
Baranzini, S. E., et al., "Network-based multiple sclerosis pathway analysis with GWAS data from 15,000 cases and 30,000 controls", American Journal of Human Genetics: A Record of Research, Review and Bibliographic Material Relating to Heredity in Man 92, (2013), 854-865.
Bloom, J. S., et al., "Finding the sources of missing heritability in a yeast cross", Nature, 494, (2013), 234-237.
Boldyrev, A., et al., "Carnosine Increases Efficiency of DOPA Therapy of Parkinson's Disease: A Pilot Study", Rejuvenation Res., 11(4), (2008), 1-8.

(Continued)

Primary Examiner — G Steven Vanni
(74) Attorney, Agent, or Firm — Schwegman Lundberg & Woessner, P. A.

(57) ABSTRACT

Disclosed in some examples are methods including selecting a first plurality of single gene mutants from a pool of possible single gene mutants of an organism. The first plurality of single gene mutants is less than a number of possible single mutants. A computer processor is used to iteratively select a second plurality of single gene mutants by selecting single gene mutants from the pool of possible single gene mutants that increases a sum of products of similarities between the first plurality of single gene mutants and corresponding functional relationships. The second plurality of single gene mutants is larger in number than the first plurality of single gene mutants, and wherein the second plurality of single gene mutants is less than the number of possible single gene mutants of the organism. A set of genes is outputted comprising the first and second pluralities of single gene mutants.

22 Claims, 12 Drawing Sheets

(56) References Cited

OTHER PUBLICATIONS

Brown, A. A., et al., "Genetic interactions affecting human gene expression identified by variance association mapping", eLife 3:e01381, (2014), 16 pgs.
Burton, P. R., et al., "Genome-wide association study of 14,000 cases of seven common diseases and 3,000 shared controls", Nature, 447, (2007), 661-678 (23 pgs.).
Califano, A., et al., "Leveraging models of cell regulation and GWAS data in integrative network-based association studies", Nature Genetics, 44, (2012), 841-847.
Cantor, R. M., et al., "Prioritizing GWAS Results: A Review of Statistical Methods and Recommendations for Their Application", American Journal of Human Genetics, 86, (2009), 6-22.
Cardon, L. R., et al., "Population stratification and spurious allelic association", The Lancet, 361(9357), (2003), 598-604.
Chiu, T., et al., "The treatment of glioblastoma multiforme through activation of microglia and TRAIL induced by rAAV2-mediated IL-12 in a syngeneic rat model", Journal of Biomedical Science, 19:45, (2012), 15 pgs.
Cordell, H. J., et al., "Detecting gene-gene interactions that underlie human diseases", Nature Reviews Genetics, 10(6), (2009), 392-404.
Cordell, H. J., et al., "Epistasis: what it means, what it doesn't mean, and statistical methods to detect it in humans", Human Molecular Genetics, 11(20), (2002), 2463-2468.
De Cid, R., et al., "Deletion of the late cornified envelope LCE3B and LCE3C genes as a susceptibility factor for psoriasis", Nature Genetics, 41, (2009), 211-215.
De Lau, L. M. L., et al., "Dietary fatty acids and the risk of Parkinson disease: the Rotterdam study", Neurology, 64, (2005), 2040-2045.
Do, C. B., et al., "Web-Based Genome-Wide Association Study Identifies Two Novel Loci and a Substantial Genetic Component for Parkinson's Disease", PLoS Genetics 7(6), e1002141, (Jun. 2011), 1-14.
Eichler, E. E., et al., "Missing heritability and strategies for finding the underlying causes of complex disease", Nature Reviews Genetics, 11, (2010), 446-450.
Fung, H. C., et al., "Genome-wide genotyping in Parkinson's disease and neurologically normal controls: first stage analysis and public release of data", The Lancet Neurology, 5, (2006), 911-916.
Gao, X., et al., "Gene-Gene Interaction Between FGF20 and MAOB in Parkinson Disease", Annals of Human Genetics, 72(2), (2008), 157-162.
Growdon, J. H., et al., "Effects of oral L-tyrosine administration on CSF tyrosine and homovanillic acid levels in patients with Parkinson's disease", Life Sciences, 30(10), (1982), 827-832.
Haavik, J., et al., "Tyrosine Hydroxylase and Parkinson's Disease", Mol Neurobiol, 16(3), (1998), 285-309.
Hamza, T. H., et al., "Common genetic variation in the HLA region is associated with late-onset sporadic Parkinson's disease", Nature Genetics, 42, (2010), 781-785.
Hamza, T. H., et al., "The heritability of risk and age at onset of Parkinson's disease after accounting for known genetic risk factors", Journal of Human Genetics, 55, (2010), 241-243.
Hanisch, U. K., "Microglia: active sensor and versatile effector cells in the normal and pathologic brain", Nature Neuroscience, 10, (2007), 1387-1394.
Hannum, G., et al., "Genome-Wide Association Data Reveal a Global Map of Genetic Interactions among Protein Complexes", PLoS Genetics, 5(12): e1000782, (Dec. 2009), 1-11.
Hemani, G., et al., "Detection and replication of epistasis influencing transcription in humans", Nature, 508(7495), (2014), 249-253.
Herold, C., et al., "INTERSNP: genome-wide interaction analysis guided by a priori information", Bioinformatics, 25(24), (2009), 3275-3281.
Hipkiss, A. R., et al., "Aging risk factors and Parkinson's disease: contrasting roles of common dietary constituents", Neurobiol Aging, 35, (2013), 1469-1472.
Hirsch, E. C., et al., "Glial Cells and Inflammation in Parkinson's Disease: A Role in Neurodegeneration?", Annals of Neurology, vol. 44, Issue 51, (Sep. 1998), S115-S120.
Hirsch, E., et al., "Melanized dopaminergic neurons are differentially susceptible to degeneration in Parkinson's disease", Nature, 334, (1988), 345-348.
Hirschhorn, J. N., et al., "Genome-Wide Association Studies for Common Diseases and Complex", Nature Reviews Genetics vol. 6, (Feb. 2005), 95-108.
Holmans, P., et al., "Gene ontology analysis of gwa study data sets provides insights into the biology of bipolar disorder", American Journal of Human Genetics, 85, (2009), 13-24.
Horn, T., et al., "Mapping of signaling networks through synthetic genetic interaction analysis by RNAi", Nature Methods, 8(4), (Apr. 2011), 341-346.
Joshi-Tope, G., et al., "Reactome: a knowledgebase of biological pathways", Nucleic Acids Research, 33, (2005), D428-D432.
Kanehisa, M., et al., "KEGG for integration and interpretation of large-scale molecular datasets", Nucleic Acids Research, vol. 40, Issue D1, (2012), D109-D114.
Kanehisa, M., "KEGG: kyoto encyclopedia of genes and genomes", Nucleic Acids Res, 28(1), (2000), 27-30.
Kannarkata, G. T., et al., "The Role of Innate and Adaptive Immunity in Parkinson's Disease", Journal of Parkinson's Disease, 3(4), (2013), 493-514.
Kelley, R., et al., "Systematic interpretation of genetic interactions using protein networks", Nature Biotechnology, 23, (2005), 561-566.
Lambert, J.-C., et al., "Meta-analysis of 74,046 individuals identifies 11 new susceptibility loci for Alzheimer's disease", Nature Genetics, 45, (2013), 1452-1458.
Lappalainen, T., et al., "Transcriptome and genome sequencing uncovers functional variation in humans", Nature, 501, (2013), 506-511.
Lehner, B., et al., "Systematic mapping of genetic interactions in Caenorhabditis elegans identifies common modifiers of diverse signaling pathways", Nature Genetics, 38(8), (Sep. 2006), 896-903.
Li, J. Z., et al., "Worldwide Human Relationships Inferred from Genome-Wide Patterns of Variation", Science, 319(5866), (2008), 1100-1104.
Lull, M. E., et al., "Microglial Activation and Chronic Neurodegeneration", Neurotherapeutics 7(4), (2010), 354-65.
Maher, B., et al., "Personal genomes: The case of the missing heritability.", Nature, 456, (2008), 18-21.
Mamtani, M., et al., "Association of copy number variation in the FCGR3B gene with risk of autoimmune diseases", Genes and Immunity, 11, (2009), 155-160.
Manolio, T. A., et al., "Finding the missing heritability of complex diseases", Nature, 461, (2009), 747-753.
Martin, M. P., et al., "Epistatic interaction between KIR3DS1 and HLA-B delays the progression to AIDS", Nature Genetics, 31, (2002), 429-434.
Mootha, V. K., et al., "PGC-1a-responsive genes involved in oxidative phosphorylation are coordinately downregulated in human diabetes", Nature Genetics, 34(3), (2003), 267-273.
Muenter, M., et al., "Patterns of dystonia ("I-D-I" and "D-I-D-") in response to I-dopa therapy for Parkinson's disease", Mayo Clin Proc., 52(3), (1977), 163-174.
Ogata, H., et al., "KEGG: Kyoto Encyclopedia of Genes and Genomes", Nucleic Acids Research, 27(1), (1999), 29-34.
Pankratz, N., et al., "Meta-analysis of Parkinson disease: Identification of a novel locus, RIT2", Annals of Neurology, 71(3), (2012), 370-384.
Park, W.-R., et al., "CD28 costimulation is required not only to induce IL-12 receptor but also to render janus kinases/STAT4 responsive to IL-12 stimulation in TCR-triggered T cells", European Journal of Immunology, 31(3), (2001), 1456-1464.
Pharoah, P. D., et al., "GWAS meta-analysis and replication identifies three new susceptibility loci for ovarian cancer", Nature Genetics, 45, (2013), 362-370.
Prabhu, S., et al., "Ultrafast genome-wide scan for SNP-SNP interactions in common complex disease", Genome Research, 22, (2012), 2230-2240.

(56) References Cited

OTHER PUBLICATIONS

Purcell, S., et al., "PLINK: A Tool Set for Whole-Genome Association and Population-Based Linkage Analyses", The American Journal of Human Genetics, 81(3), (2007), 559-575.

Quinlan, A. R., et al., "BEDTools: a flexible suite of utilities for comparing genomic features", Bioinformatics 26(6), (2010), 841-842.

Rabinowitz, D, et al., "A unified approach to adjusting association tests for population admixture with arbitrary pedigree structure and arbitrary missing marker information", (Abstract), Human Heredity, 50(4), (2000), 211-223, (2000), 1 pg.

Ritchie, M. D., et al., "Multifactor-Dimensionality Reduction Reveals High-Order Interactions among Estrogen-Metabolism Genes in Sporadic Breast Cancer", American Journal of Human Genetics, 69(1), (2001), 138-147.

Rogers, J., et al., "Neuroinflammation in Alzheimer's disease and Parkinson's disease: are microglia pathogenic in either disorder?", International Review of Neurobiology, 82, (2007), 235-246.

Sekeris, C. E., et al., "Zum tyrosinstoffwechsel der insekten VII. Der katabolische abbau des tyrosins und die biogenese der sklerotisierungs-substanz, N-acetyl-dopamin", (w/ English Summary), Biochimica et Biophysica Acta, 62, (1962), 103-113.

Simon-Sanchez, J., et al., "Genome-wide association study reveals genetic risk underlying Parkinson's disease", Nature Genetics, 41, (2009), 1308-1312.

Stahl, E. A., et al., "Bayesian inference analyses of the polygenic architecture of rheumatoid arthritis", Nature Genetics, 44(3), (May 2012), 483-489 (9 pgs.).

Storey, J. D., et al., "Multiple Locus Linkage Analysis of Genomewide Expression in Yeast", PLoS Biology, 3(8): e267, (2005), 1380-1390.

Subramanian, A., et al., "Gene set enrichment analysis: a knowledge-based approach for interpreting genome-wide expression profiles", Proc. Natl. Acad. Sci. USA, 102(43):, (2005), 15545-1550.

Taoufik, Y., et al., "Human microglial cells express a functional IL-12 receptor and produce IL-12 following IL-12 stimulation", European Journal of Immunology, 31, (2001), 3228-3239.

Tong, A. H. Y., et al., "Global Mapping of the Yeast Genetic Interaction Network", Science, vol. 303, (2004), 808-813.

Vom Berg, J., et al., "Inhibition of IL-12/IL-23 signaling reduces Alzheimer's disease-like pathology and cognitive decline", Nature Medicine, 18(12), (Dec. 2012), 1812-1819.

Walter, L., et al., "Role of microglia in neuronal degeneration and regeneration", Seminars in Immunopathology, 31, (2009), 513-525.

Wan, X., et al., "BOOST: A Fast Approach to Detecting Gene-Gene Interactions in Genome-wide Case-Control Studies", The American Journal of Human Genetics, 87, (2010), 325-340.

Wang, K., et al., "Analysing biological pathways in genome-wide association studies", Nature Reviews Genetics, 11, (2010), 843-854.

Wang, K., et al., "Pathway-based approaches for analysis of genomewide association studies", The American Journal of Human Genetics, 81(6), (Dec. 2007), 1278-1283.

Warrington, K. J., et al., "CD28 loss in senescent CD4+ T cells: reversal by interleukin-12 stimulation", Blood, 101(3), (2002), 3543-3549.

Watford, W. T., et al., "The biology of IL-12: coordinating innate and adaptive immune responses", Cytokine & Growth Factor Reviews, 14, (2003), 361-368.

Welter, D., et al., "The NHGRI GWAS Catalog, a curated resource of SNP-trait associations", Nucleic Acids Research, 42, (2014), D1001-D1006.

Wu, M. C., et al., "Rare-Variant Association Testing for Sequencing Data with the Sequence Kernel Association Test", The American Journal of Human Genetics, 89(1), (2011), 82-93.

Zhang, B., et al., "Integrated Systems Approach Identifies Genetic Nodes and Networks in Late-Onset Alzheimer's Disease", Cell, 153(3), (2013), 707-720.

Zhang, F., et al., "Epistasis analysis for quantitative traits by functional regression model", Genome Research, 24(6), (2014), 989-998.

Zuk, O., et al., "Searching for missing heritability: Designing rare variant association studies", Proc. Natl. Acad. Sci. USA, 111(4), (2014), E455-E464.

Zuk, O., et al., "The mystery of missing heritability: Genetic interactions create phantom heritability", Proc. Natl. Acad. Sci. USA, 109(4), (2012), 1193-1198.

"International Application Serial No. PCT/US2017/022308, International Preliminary Report on Patentability dated Sep. 27, 2018", 9 pgs.

"U.S. Appl. No. 16/079,664, Preliminary Amendment filed Aug. 24, 2018", 7 pgs.

SCREENING OF LARGE-SCALE GENETIC INTERACTION NETWORKS

CROSS-REFERENCE TO RELATED APPLICATION

This application claims the benefit of priority to U.S. Provisional Patent Application Ser. No. 62/317,038 entitled "OPTIMAL SCREENING OF LARGE-SCALE GENETIC INTERACTION NETWORKS," filed Apr. 1, 2016, the disclosure of which is incorporated herein in its entirety by reference.

GOVERNMENT RIGHTS

This invention was made with Government support under 1R01HG005084 and 1R01GM104975-01 awarded by The National Institutes of Health (NIH). The Government has certain rights in the invention.

TECHNICAL FIELD

Embodiments pertain to large-scale genetic interaction screenings. Some embodiments relate to the use of computer algorithms to develop efficient strategies for testing genetic interactions.

BACKGROUND

Genetic interactions are a powerful means of understanding how genomes are functionally organized. Genetic interactions have been systematically screened in several organisms by conducting simultaneous perturbations on two or more genes and comparing the resultant phenotype to a phenotype derived from expecting independence between the genes' perturbations.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
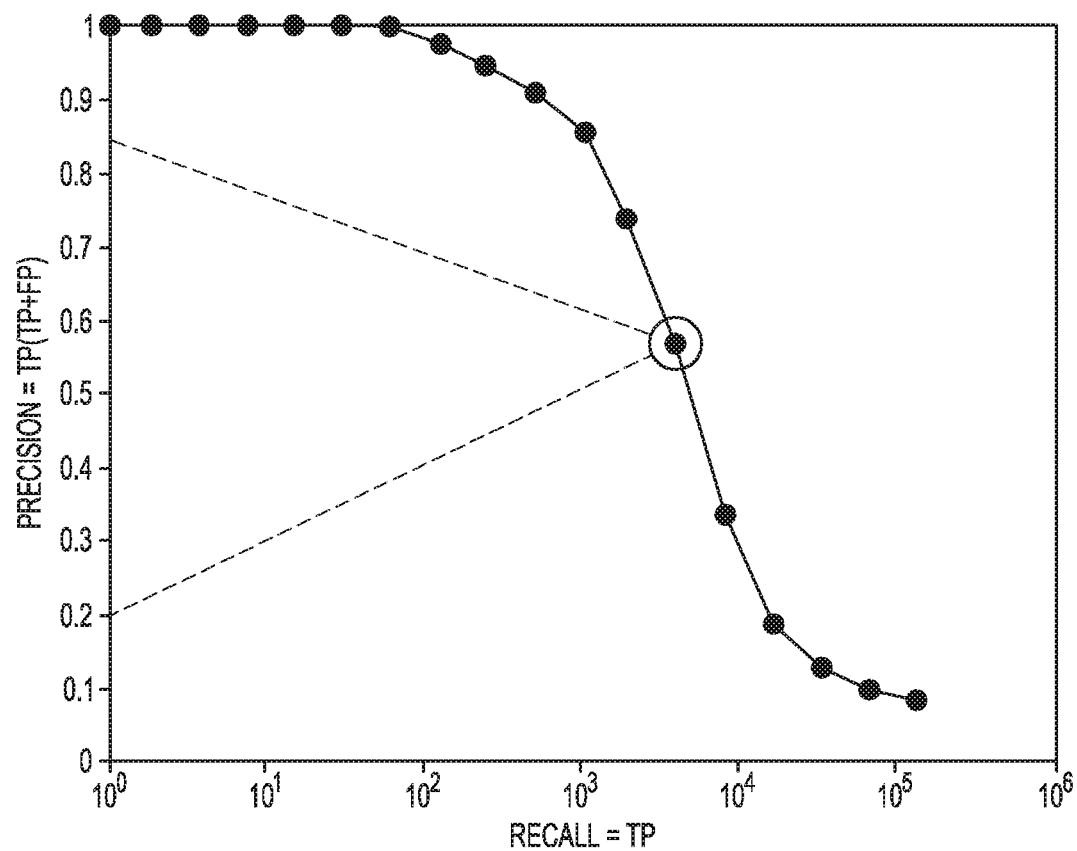
FIG. 1 is a chart and diagram showing that the information content in the genetic interaction profile similarity network is captured by a precision-recall curve, according to some examples of the present disclosure.

Due to the utility of genetic interactions and advances in high-throughput genomic technology, genetic interaction screens are becoming increasingly important. Interaction screens can be applied to new dimensions including different time points, organisms, physical and chemical conditions, alleles of genes, and higher level interactions. While screening has been conducted across all pairs of genes for genetic interactions in *S. cerevisiae* and while forays have been made into screening new dimensions, conducting exhaustive screening across the complete space of all these new dimensions is resource intensive and is often infeasible, particularly in larger genomes or multicellular organisms.

While screening optimization has been reported in some contexts such as protein-protein interaction screens, the results in some cases do not readily apply to genetic interaction due to its unique behavior and usage. This uniqueness can necessitate a systematic study of different approaches and development of new methods for genetic interaction specific use cases. Some attempts have been made to optimize the screening for some of the genetic interaction use cases in the past. For example, genes with low single mutant fitness have been prioritized for screening when it became clear that these genes were hubs in the genetic interaction network. Another heuristic popularly used in the community is to pick representative genes spanning across all known functional categories. Another example method proposed to solve this problem is by prioritizing genes with least uncertainty, that is, genes that clearly belong to a functional cluster. Another example of heuristic uses the standard deviation of the genetic interaction profiles. However, no study or analyses have been conducted to devise and evaluate strategies for several other use cases including genetic interaction profile similarity.

There are several ways the genetic interaction data can be operationally used. Some examples of the ways genetic interactions are used include (i) discovering similar genes by finding gene pairs with similar genetic interaction profiles (profile similarity), (ii) discovering important genes in the genome by finding hubs in genetic interaction networks (hub estimation), (iii) discovering pathway-level interactions by identifying local structure in the genetic interaction network (network structure), and (iv) using direct genetic interactions for specialized cases such as cancer synthetic lethality (interaction coverage). Devising screening strategies to optimize the information content for these use cases can also apply to several other genetic interaction applications.

Disclosed in some examples are systems, methods, and machine readable mediums for determining screens that can efficiently achieve objectives formulated for each of these use cases with a small number of screens. To demonstrate the impact of screen prioritization, one of the approaches disclosed herein for optimal selection of screens for functional profiling is applied to support a large-scale chemical genomics screen. Optimal selection is the selection of a subset of all the possible genes that maximizes the number of interactions discovered or the amount of functional information contained therein while minimizing the number of genes to screen. Thus, adding more mutants to an optimally selected set of mutants for a screen is expected not to add significantly more information, in a statistical sense, beyond the optimal mutant set. For example, the optimal number of the genes to be selected may be decided based on where precision at 25% recall averaged across different functional categories peaks. Optimization in this context can account for a nearly 10-fold speed-up in the rate at which interactions can be screened while retaining, and even improving, the amount of information extracted from the screen.

Complete screening of genetic interaction networks can be important for model organisms as it can provide a reference for other chemical genomics and condition specific genetic interaction studies. To provide these references, exhaustive screening combining all pairs of possible mutations in several model organisms including *S. cerevisiae* and *E. coli* have been studied. However, there are several contexts such as chemical genomics and condition-specific genetic interaction experiments, where complete screening may be prohibitive because the condition dimension or the chemical compounds space can be very large. Furthermore, as screening technologies are applied in higher organisms, the disclosed systems, methods, and algorithms may be used to prioritize and dramatically increase the information in the dataset even with few screens.

Two general screening strategies used for genetic interaction screening in species include the rectangular screen design and square design. The rectangular approach refers to the scenario where query gene mutant strains are crossed against a complete (or near-complete) deletion collection. When several query genes are screened against the complete deletion collection, this creates a rectangular genetic interaction matrix. The square approach involves screening a small set of genes against the same set of genes on the array side, an approach which has been adopted in several cases to rapidly cover small sets of functionally related genes. Using the methods, algorithms, and systems described herein, only a small number of query genes may be required to generate a useful profile similarity network. This number can be further reduced by intelligent selection of genes using the approaches described herein. Thus, the rectangular approach can give an unbiased picture on a genome scale and, at the same time, be cost effective. Further, the rectangular approach can be better suited for distributed screening efforts in which screen data from multiple labs is pooled together.

Genetic interaction profile similarities can be used for finding of functionally similar genes, validation and visualization of genetic interaction networks. Since complete genetic interaction profiles may not be required for estimation of the profile similarity network, an algorithm called COMPRESS-GI (COMpress Profiles Related to Epistasis by Selecting Informative Genes), disclosed herein can select an informative set of genes for screening to optimize the performance of the profile similarity use case. The method takes as input genetic interactions and Gene Ontology datasets and outputs an informative set of genes that maximizes the precision-recall statistics of the profile similarity network. Precision-recall statistics are a metric for measuring the information content in the genetic interaction data by comparing the profile similarity network with known gene relations. This is shown in FIG. 1, which is a line chart showing information content in the genetic interaction profile similarity network as capture by a precision-recall curve. Co-annotations from Gene Ontology are used, which is a repository of all gene annotations, to obtain an external reference or "gold standard" set of known gene relations. The objective is to select a set of genes such that the precision-recall curve of the similarity network generated from the partial profile based on those genes is maximized.

Based on this objective, a step-wise exhaustive greedy approach is used, where the most informative gene is selected, and for later iterations, a gene is picked that is the most informative gene when added to the already selected set. The process is shown generally in FIG. 2 which is flowchart describing the COMPRESS-GI method.

According to various embodiments, a set of genetic interaction data (m query genes crossed against n array genes) and a gene ontology standard for the query genes (size m by m), analyzed according to the COMPRESS-GI method can discover an informative subset of array genes. A possible objective for selecting the informative subset of genes is to maximize a match between gene profile similarities based on the selected partial profiles and gene co-annotations in Gene Ontology.

In order to quantify the matching, precision-recall statistics can be used. Precision-recall can include treating gene profile similarities as predictions and co-annotations from Gene Ontology as the gold standard positive and by treating unrelated genes in the Gene Ontology as gold standard negative. Using precession-recall, the informative set of genes can be discovered by exhaustively searching for genes that when added to the selected set of genes will best improve the precision-recall statistics.

Figure 2:
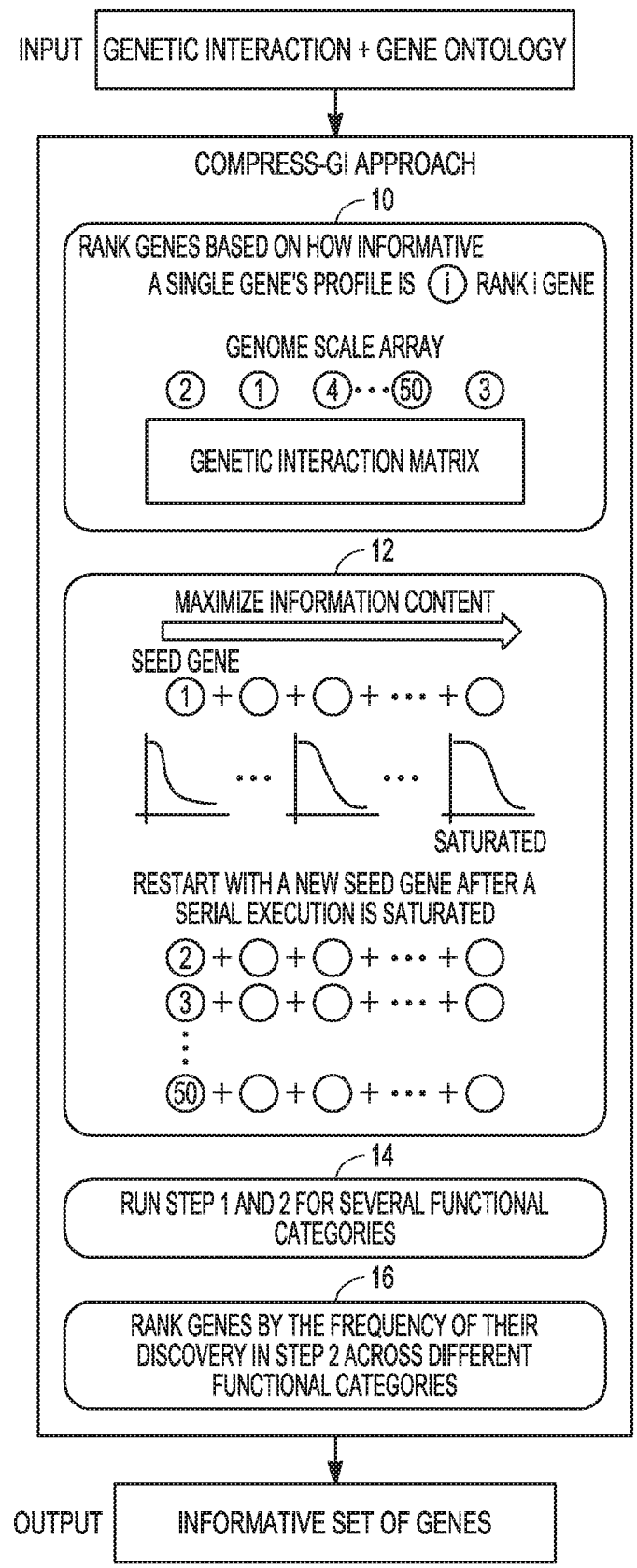
FIG. 2 shows a flowchart of the COMPRESS-GI method, which is used to select mutant strains for screening genetic interactions according to some examples of the present disclosure.

As an example with reference to FIG. 2, input is provided and ultimately an output set of informative genes is produced. At operation 10 in order to discover a first gene, an exhaustive search can be conducted of all genes present in an array. From there the gene that gives the best precision-recall statistics is selected at operation 12. The precision-recall statistic can be a way to assess both precision as well as recall of predictions against a gold standard truth. In an example of a machine learning setting, there can be a positive and a negative class which are being predicted. If a positive prediction is found correct according to the positive gold standard, then the prediction is called "True Positive" otherwise it is called "False Positive." Likewise, if a negative prediction is correct according to the negative gold standard it is "True Negative" otherwise it is "False Negative." Precision can be defined as TP/(TP+FP) and Recall as TP/(TP+FN), where TP, FP, FN are number of True Positives, False positives, and False negatives predictions respectively.

In some examples, precision-recall statistics are used to assess the match between the gene similarities based on partial profiles with co-annotations in Gene Ontology. To evaluate the predictions and compute precision gold standard positive co-annotations and gold standard negative co-annotations can be used. The similarities are thresholded at different points (recall equal to integral powers of 2 and the last recall) where precision and recall statistics are calculated and the precision-recall curve is plotted. Since the denominator for recall is constant for all similarity thresholds (TP+FN=number of is in the GO standard matrix), the denominator has been ignored and used Recall=TP.

At operation 14, after the first gene is discovered a second gene can be discovered by searching all the array genes except for the first selected gene. The second gene is the gene that gives best precision-recall statistics along with the first gene. This process can be continued until the precision-recall statistic saturates and the increase by adding any gene does not increase the precision-recall statistic significantly. While not so limited, about 10 to about 10,000, genes can be selected before the precision-recall statistic saturates, or about 10 to about 1,000, about 15 to about 500, or about 15 to about 25 genes can be selected. In many applications only a subset of genes from the genome need to be selected in order to achieve sufficient precision recall values.

The genes that are selected during the course of the COMPRESS-GI method can be influenced by genes already selected by the method. For example, a different starting gene may give different sets of informative genes. Therefore, in some embodiments to make sure that the genes selected are robust to the selections of the starting gene, the COMPRESS-GI algorithm can run with different starting genes. For example, instead of starting with the best gene as the first gene, in some examples, the method can start with the second best gene and the first gene is allowed to occur in the COMPRESS-GI selections. This process can be repeated with each of the 50 best genes ranked high in the precision-recall statistics based on the single gene profile as starting gene.

Further, to make sure that all the major functional categories are represented by the selected set of genes, the COMPRESS-GI algorithm can be repeated for several different functional contexts. The functional context can be created by limiting the Gene Ontology standard to only genes that are related to the function.

Figure 3:
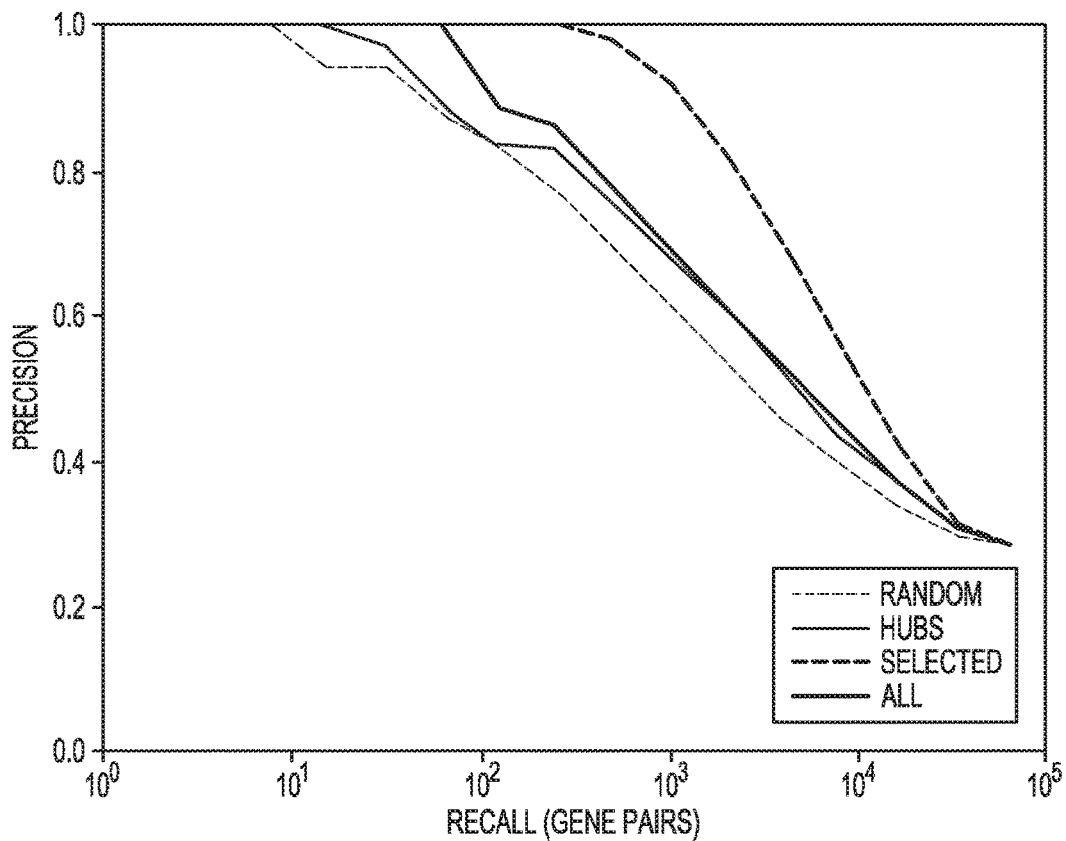
FIG. 3 is a chart showing the evaluation of (*S. pombe*), according to some examples of the present disclosure.

The different sets of genes obtained by running with different start genes and in different functional contexts can be combined and the genes can be sorted by their frequency of occurrence in these sets. In some examples, the optimal number of the genes to be selected can be decided based on where precision at about 15%, 20%, 25%, 30%, or 35% recall averaged across different functional categories peaks. This is shown in FIG. 3 which is a plot showing the % recall.

At operation 16, for the COMPRESS-GI approach, precision recall curves can be compared to find the best gene to select at each iteration. The precisions can be compared at recall equal to powers of 2. The precisions at earlier powers of 2 are compared first. If one of the PR curves has higher precision at that recall, that one is considered to be a better PR curve. In case of tie, precisions at higher recalls are considered. In some examples, after the PR curve has saturated, even weak profiles may become slightly better by chance. To safeguard against this situation, in addition to checking that the PR curve improves the increase may be checked to determine if it is greater than the sum of standard error in the two precisions. Given precision p=TP/(TP+FP), where TP, FP are number of true positive and false positives, respectively, the standard error on p is calculated as $$\sqrt{\frac{p(1-p)}{TP+FP}}.$$

The COMPRESS-GI can be run at several different functional contexts, meaning informative set of genes can be selected for the different functional category. To compute category specific precision-recall statistics and optimize on that objective, the Gene Ontology (GO) standard can be modified to be specific to the functional category. The GO standard. M, can be changed as follows:
  (1) $M_{i,j}$ is unchanged if genes i, j both belong to the functional category,
  (2) $M_{i,j}=0$ if originally $M_{i,j}=1$ and only one of the genes i, j belong to the functional category.
  (3) $M_{i,j}$ is unchanged if $M_{i,j}=-1$ originally The GO standard for the genes within the functional category remain unchanged (1), but co-annotations of gene pairs outside the functional category are set to 0. Even though the focus of the optimization is to select genes informative for a particular functional context, the −1 s in GO standard are not changed so that predicting unrelated genes as related is penalized.

The complexity of this algorithm can be a function of the complexity of calculating a precision recall curve, which is repeated the size of the array (n) multiplied by number of genes picked in each run (average a=10). Also, each of the runs can be repeated for different start genes (fraction of array size) and for different functional contexts (f). The main contributor for the complexity in precision-recall statistics can be the sorting of the query gene similarities. The computation of the gene similarity takes $O(am^2)$ time and sorting of m C 2 similarities take O(m² log m) time. In total, the algorithm has complexity of O(am²+m² log m)(a)(n)(f)(n)=O(m²n2(a+log m)af).

The sorting of the gene similarities can be the most expensive part of the algorithm. A possible way of mitigating this expense is instead of sorting the entire list of query gene similarities, sorting only the top 100,000 gene similarities. Finding the 100.000th largest number is an O(m²) operation, which can be further implemented in the C programming language to increase the speed. Similarities greater than the 100,000th largest similarity are considered and sorted. As described, 100,000 is a small fraction of the m² so it does not change the complexity of the algorithm but the run time is greatly improved.

Figure 4:
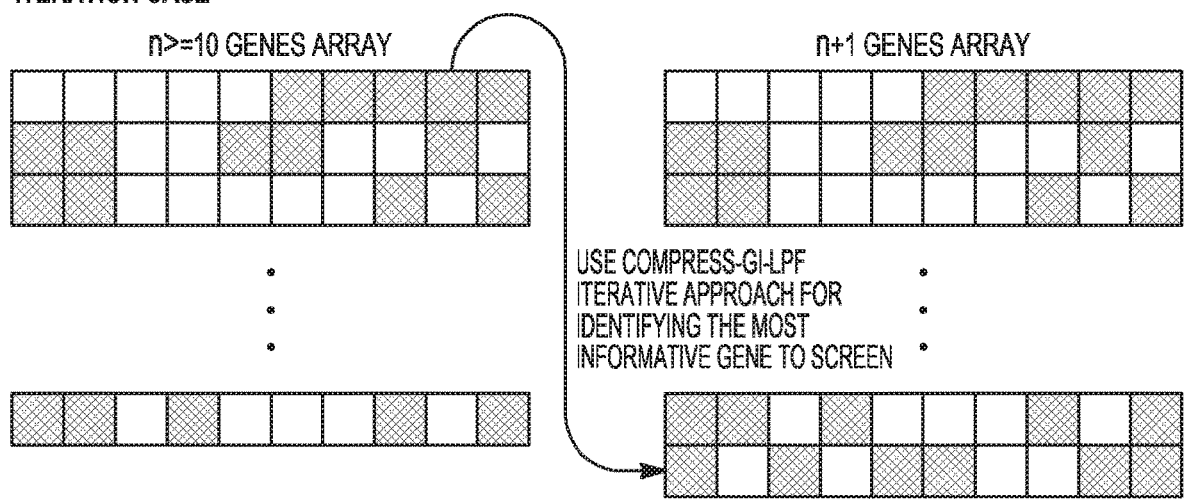
FIG. 4 is a schematic showing the iterative genetic interaction screening scenario for which COMPRESS-GI-LAF was developed according to some examples of the present disclosure.

The informative set of genes in COMPRESS-GI can be well-suited for applications such as chemical genomics screens and condition-specific genetic interaction screening. However, the algorithm in some examples, takes as input a sizeable genetic interaction matrix. For a de novo genetic interaction screening scenario, an iterative LAF (COMPRESS-GI Linear Algebra Formulation) approach can be used to prioritize genes. This is shown in FIG. 4 which is a schematic describing the iterative genetic screening scenario, as applied to COMPRESS-GI-LAF which is disclosed herein.

This method may be useful for genetic interaction screening in new organisms and also for new conditions in already established model organisms. The LAF approach is an approximation of the COMPRESS-GI approach but is orders of magnitude faster. LAF optimizes the sum of products of similarities between genes and their known GO co-annotations between them (0, 1, or −1), which can be summarized as Hadamard's product or element-wise matrix multiplication. Using properties of the trace on Hadamard's product along with the cyclic property of the trace product of matrices, the problem can be reduced to a 0-1 knap-sack problem, giving each gene a score that is related to the gene's informativeness. The genes can be ranked by their scores and top genes can be selected and screened.

Given its computational efficiency, the LAF approach can be suited for the iterative genetic interaction screening scenario where screens are selected in an online fashion after each additional screen. For comparison, a baseline approach has been developed: iterative hubs, which is based on screening the highest-degree unscreened hub after each screen.

The LAF method is also based on a similar objective of optimizing the match between the similarities of the genes with Gene Ontology standard (G). The similarities of the genes based on the partial profiles can be written as $XW(XW)^T = XWW^TX^T = XWX^T$ where X is the genetic interaction at the current iteration W is the diagonal matrix with $W_{ii}=1$ if array gene i is selected. However, unlike COMPRESS-GI where precision-recall statistics are used to assess the match between $XWX^T$ and G, the sum of element wise multiplication of $XWX^T$ and G is optimized on. This objective can be written as:

$$\max_W \text{ sum of matrix elements } (XWX^T \odot G)$$

(where ⊙ is the element wise multiplication and more formally known as Hadamard product)

$$= \max_W e^T(XWX^T \odot G)e \text{(sum of element in matrix } M = e^T Me\text{)}$$

$$= \max_W e^T(A \odot G)e \text{(Let } A = XWX^T\text{)}$$

$$= \max_W tr(D_e^* A D_e G^T) \text{(property of Hadamard product)}$$

$$= \max_W tr(AG^T)$$

$$= \max_W tr(XWX^T G^T)$$

$$= \max_W tr(G^T XWX^T)$$

$$= \max_W tr(X^T G^T XW)$$

$$= \max_W (X^T G^T X)_{ii} * W_{ii}$$

This process reduces the problem to a type of 0-1 knapsack problem which can be solved by a greedy algorithm. Briefly stated, a knapsack problem is a problem in which given a set of items, each with a weight and a value, the number of each item to include in a collection is determined so that the total weight is less than or equal to a given limit and the total value is as large as possible. To solve this problem, the genes are ranked by $(X^T G^T X)_{ii}$ and the top n genes are picked.

The complexity of this algorithm mainly lies in the matrix multiplication $X^T G^T X$. So if X is the genetic interaction matrix composed of m queries and n arrays, the complexity for $X^T$ $G^T X$ matrix multiplication is O(nmm)+(nmn)=O((mn)(m+n)). The complexity of the knapsack problem is O(n), so the overall complexity of the algorithm is O((mn)(m+n)). This complexity makes the algorithm perfectly reasonable to run on genetic interaction datasets that are several folds larger than the current largest genetic interaction datasets. Further, the algorithm can be used even for organisms with a much larger number of genes for example where m.n is in a ranger from about 10.000 to about 500,000 about 50.000 to about 450.000, about 100,000 to about 400,000, about 150,000 to about 350.000, or about 200.000 to about 300.000). This complexity can allow the algorithm to be run very quickly for iterative approaches.

Figure 5:
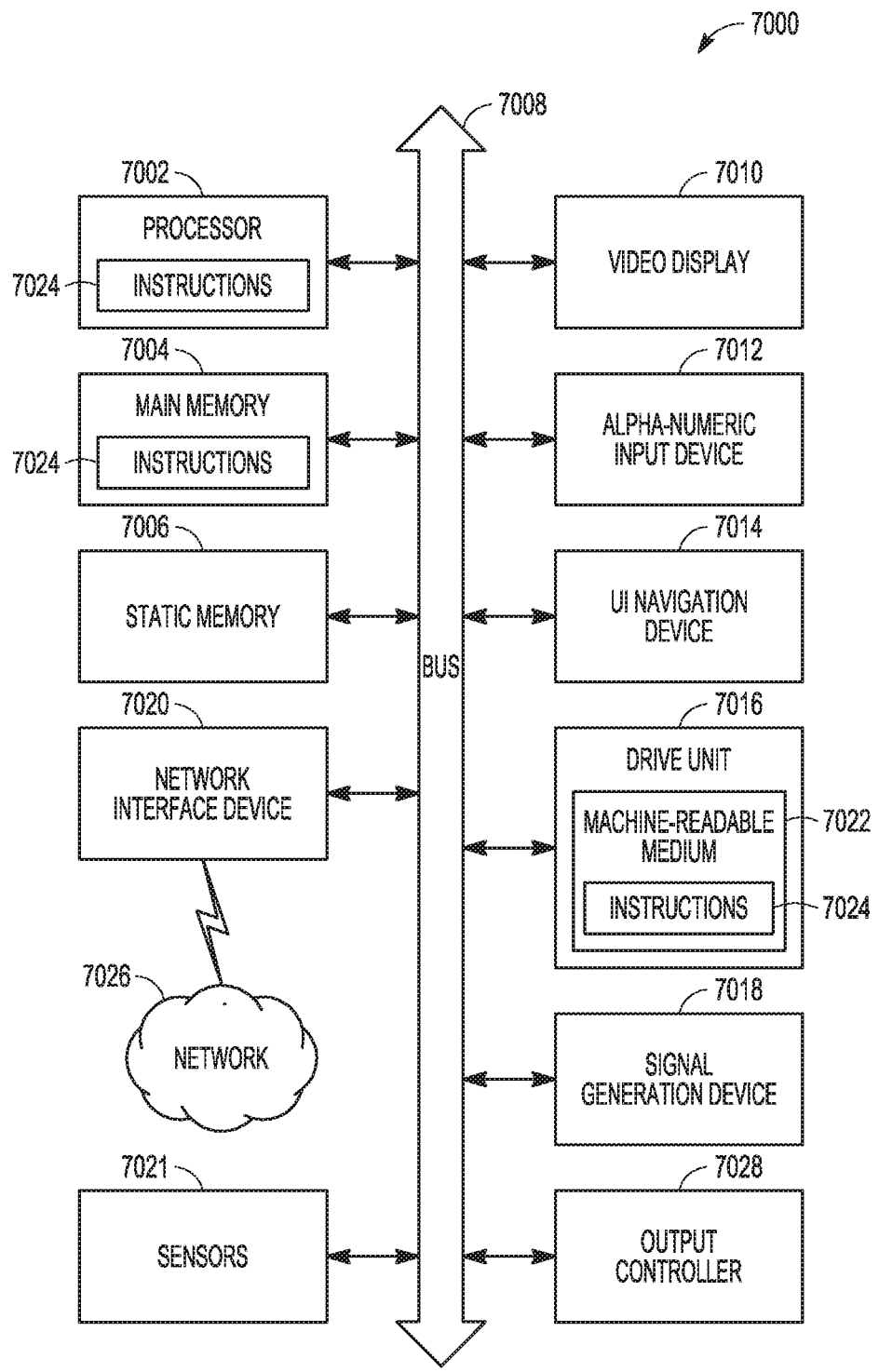
FIG. 5 is a block diagram illustrating an example of a machine upon which one or more embodiments may be implemented according to some examples of the present disclosure

FIG. 5 illustrates a block diagram of an example machine 7000 upon which any one or more of the techniques (e.g., methodologies) discussed herein may perform. For example, the machine 7000 may be configured to perform the COMPRESS-GI algorithm or the LAF algorithms. In alternative embodiments, the machine 7000 may operate as a stand-alone device or may be connected (e.g., networked) to other machines. In a networked deployment, the machine 7000 may operate in the capacity of a server machine, a client machine, or both in server-client network environments. In an example, the machine 7000 may act as a peer machine in peer-to-peer (P2P) (or other distributed) network environment. The machine 7000 may be a personal computer (PC), a tablet PC, a set-top box (STB), a personal digital assistant (PDA), a mobile telephone, a smart phone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 7000 may include a hardware processor 7002 (e.g., a central processing unit (CPU), a graphics processing unit (GPU), a hardware processor core, or any combination thereof), a main memory 7004 and a static memory 7006, some or all of which may communicate with each other via an interlink (e.g., bus) 7008. The machine 7000 may further include a display unit 7010, such as a graphical user interface, an alphanumeric input device 7012 (e.g., a keyboard), and a user interface (UI) navigation device 7014 (e.g., a mouse). In an example, the display unit 7010, input device 7012 and UI navigation device 7014 may be a touch screen display. The machine 7000 may additionally include a storage device (e.g., drive unit) 7016, a signal generation device 7018 (e.g., a speaker), a network interface device 7020, and one or more sensors 7021, such as a global positioning system (GPS) sensor, compass, accelerometer, or other sensor. The machine 7000 may include an output controller 7028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 7016 may include a machine readable medium 7022 on which is stored one or more sets of data structures or instructions 7024 (e.g., software) embodying or utilized by any one or more of the techniques or functions described herein. The instructions 7024 may also reside, completely or at least partially, within the main memory 7004, within static memory 7006, or within the hardware processor 7002 during execution thereof by the machine 7000. In an example, one or any combination of the hardware processor 7002, the main memory 7004, the static memory 7006, or the storage device 7016 may constitute machine readable media.

While the machine readable medium 7022 is illustrated as a single medium, the term "machine readable medium" may include a single medium or multiple media (e.g., a centralized or distributed database, and/or associated caches and servers) configured to store the one or more instructions 7024.

The term "machine readable medium" may include any medium that is capable of storing, encoding, or carrying instructions for execution by the machine 7000 and that cause the machine 7000 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media may include non-transitory machine readable media. In some examples, machine readable media may include machine readable media that is not a transitory propagating signal.

The instructions 7024 may further be transmitted or received over a communications network 7026 using a transmission medium via the network interface device 7020. The Machine 7000 may communicate with one or more other machines utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 7020 may include one or more physical jacks (e.g., Ethernet, coaxial, or phone jacks) or one or more antennas to connect to the communications network 7026. In an example, the network interface device 7020 may include a plurality of antennas to wirelessly communicate using at least one of single-input multiple-output (SIMO), multiple-input multiple-output (MIMO), or multiple-input single-output (MISO) techniques. In some examples, the network interface device 7020 may wirelessly communicate using Multiple User MIMO techniques.

---

SOURCE CODE LISTING. The following is an example source code listing and is not intended to be limiting.

```
function iterativeMethod( )
    addpath(genpath('utils/'));
    runIterative( ); %% important
end
function runIterative( ) % works on all
    GOstandard = load('GOstandard.mat');
    sga = getSGA_fromfolder('squareSGA');
    sga_transpose = getTranspose(sga);
```

-continued

```
        randinds = randperm(length(sga.query));
        randinds = randinds(1:10);
        selected = sga.query(randinds);
        mapping = containers.Map(sga.query, 1:length(sga.query));
        while length(selected) < length(sga.array)
        selectedinds =[ ];
        for i = 1:length(selected)
            selectedinds(i) = mapping(selected{i});
        end
            newsga = struct( );
            newsga.query = sga.query(selectedinds);
            newsga.array = sga.array;
            newsga.matrix = sga.matrix(selectedinds, :);
                next = getNext(newsga, GOstandard);
                selected = [selected; next];
            end
            length(unique(selected))
            writeGenes(selected, 'output.txt');
end
function writeGenes(selected, filename)
        fid = fopen(filename, 'w');
        for i = 1:length(selected)
            fprintf(fid, '%s\n', selected{i});
        end
end
function next = getNext(sga, GOstandard)
        mapping = containers.Map(sga.array, 1:length(sga.array));
    selectedinds =[ ];
    for i = 1:length(sga.query)
        selectedinds(i) = mapping(sga.query{i});
    end
    a = 1:length(sga.array);
    arrayinds = setdiff(a, selectedinds);
    sga1 = getSubsetSGA(sga, 1:length(sga.query), arrayinds);
    [sga1, newGOstandard] = getCompatibleSGA_GO(sga1, GOstandard);
    Y = sga1.matrix'*newGOstandard.matrix'*sga1.matrix;
    v = diag(Y);
    [~, inds] = sort(v, 'descend');
    next = sga1.array( inds(1) );
end
function newsga = getTranspose(sga)
    newsga = struct( );
    newsga.array = sga.query;
    newsga.query = sga.array;
    newsga.matrix = sga.matrix.';
end
function newsga = getSubsetSGA(sga, qinds, ainds)
    newsga = struct( );
    newsga.array = sga.array(ainds);
    newsga.query = sga.query(qinds);
    newsga.matrix = sga.matrix(qinds, ainds);
end
```

EXAMPLES

Various embodiments of the present disclosure can be better understood by reference to the following Examples which are offered by way of illustration. The present disclosure is not limited to the Examples given herein.

Example 1.1: Number of Genome Wide Genetic Interaction Screens Required for Various Genetic Interaction Use Cases To investigate how the number of genes included in a genetic interaction screen affects the utility of the resulting data for various use cases, a subset of the array genes of varying sizes was randomly selected and the performance of each application on these partial profiles was evaluated. To mimic selection from the whole non-essential genome, random subsets of genes from the array side of the *S. cerevisiae* genetic interactions were selected which included nearly the complete non-essential deletion collection.

Figure 6:
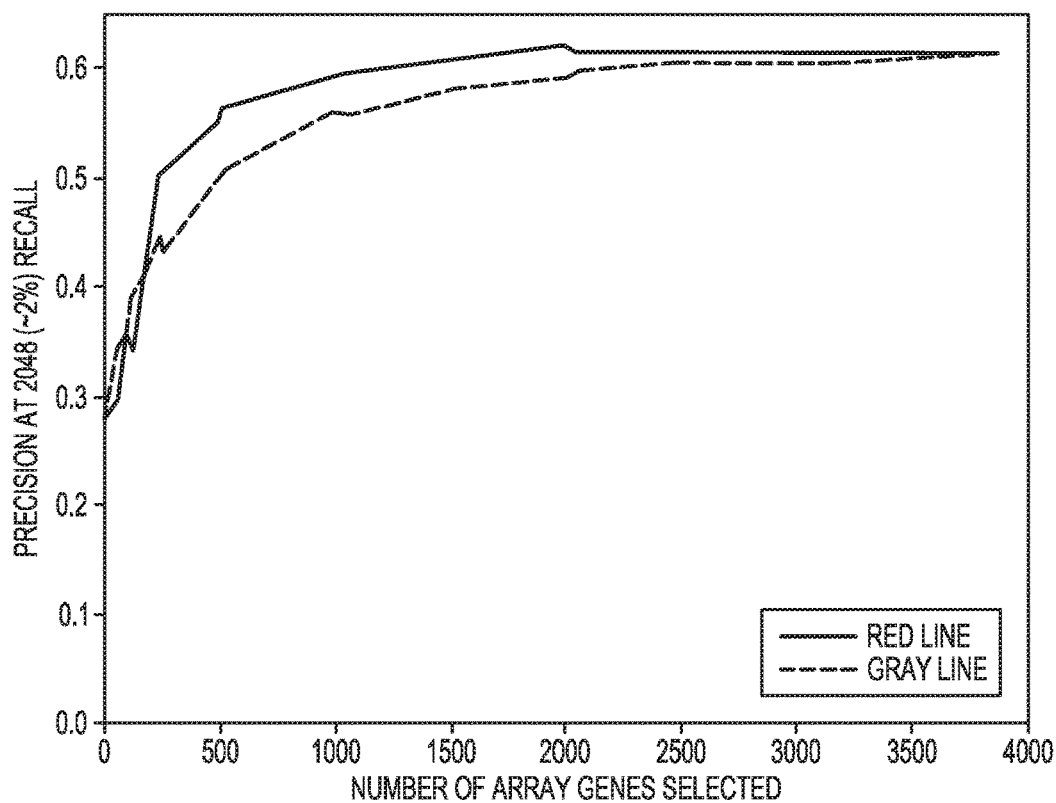
FIG. 6 is a chart showing how different selections of random genes (dashed line labeled gray line) and low single mutation fitness genes (solid line labeled red line) affect the ability to estimate a profile similarity network according to some examples of the present disclosure.
Figure 7:
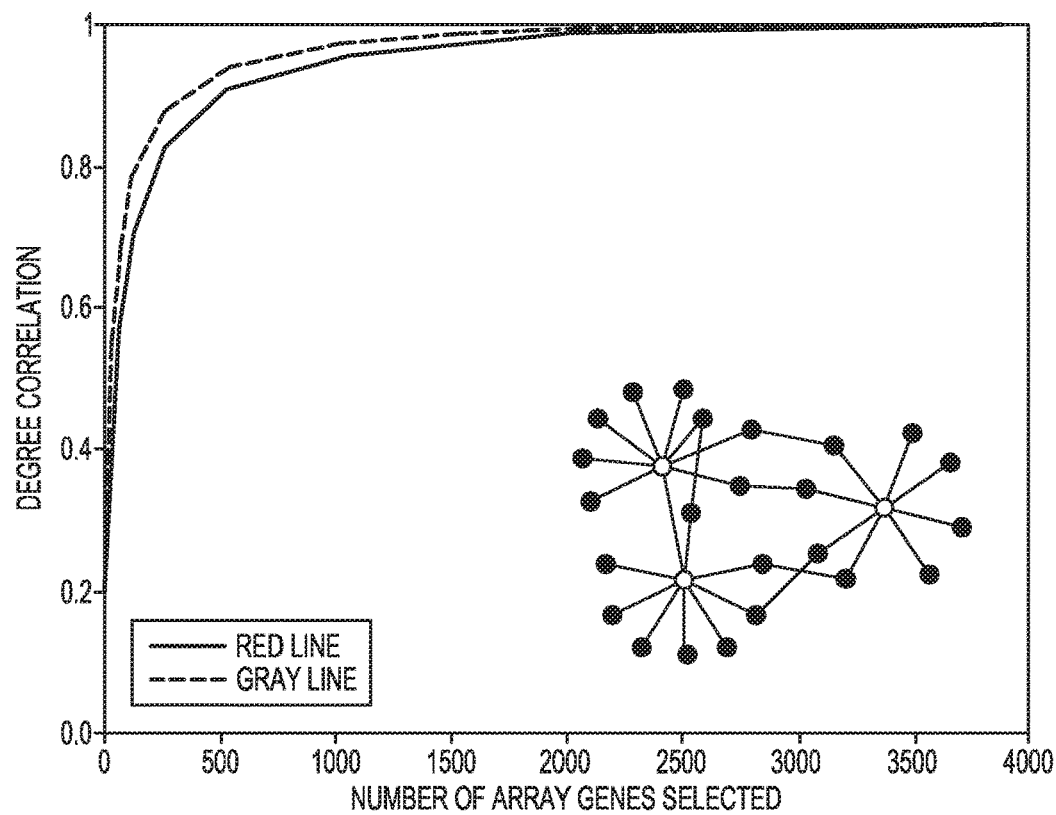
FIG. 7 is a chart showing how different selections of random genes (dashed line labeled gray line) and low single mutation fitness genes (solid line labeled red line) affect genetic interaction degree estimation according to some examples of the present disclosure.

When the genes are selected randomly, the performance of the profile similarity and degree estimation use cases increases rapidly in the beginning with diminishing improvements for later screens as the performance saturates. For instance, the performance of the profile similarity use case with just random 10% genome screened is on average around 80% of the performance with complete genome screened. This is shown in FIG. 6, which shows a profile similarity network measured using precision-recall curve. Random genes are shown with the dashed line labeled gray line and low single mutation fitness genes are shown using the solid line labeled red line. To estimate the performance for the profile similarity use case, a precision at a recall of 2048 (~2% of all annotated gene pairs) was used based on a standard of gene co-annotation of genes in the Gene Ontology. Similar to the profile similarity use case, for the degree estimation use case, a correlation of 0.8 was observed between degree estimates of genes with just 10% of the genome screened and the actual degree based on the complete genome screens. This is shown in FIG. 7 which shows a genetic interaction degree estimation with partial profiles and Pearson correlation used to compare with degrees obtained from the complete dataset. Random genes are shown with the dashed line labeled gray line and low single mutation fitness genes are shown using the solid line labeled red line. Surprisingly, screening genes with low single mutant fitness is worse for the performance of the hub prediction use case compared to a random screening strategy. This observation is also true for the profile similarity use case, where prioritizing genes by the severity of their single mutant fitness defects is worse than a random screening strategy until ~50 screens; however, they improve upon random selection for a higher number of screens.

This observation suggests that screening low single mutant fitness genes may not be a good strategy relative to the screening of random genes for the degree estimation or for the profile similarity use case for small scale studies (for screening less than 50 genes).

Figure 8:
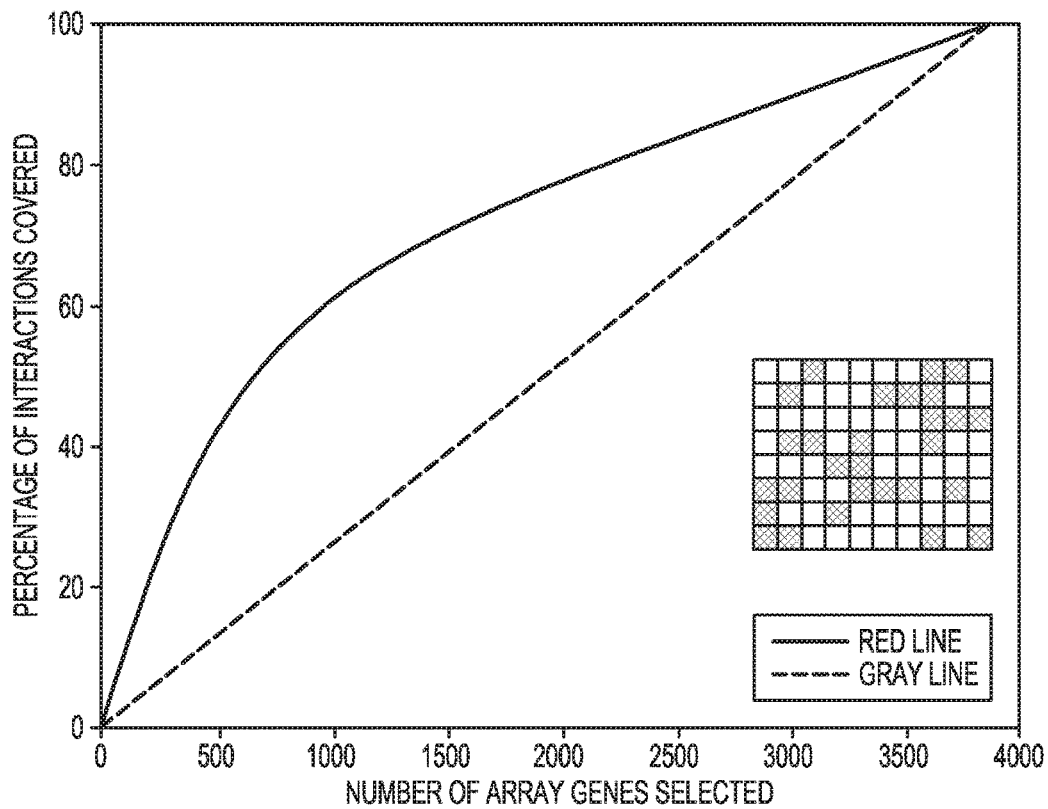
FIG. 8 is a chart showing how different selections of random genes (dashed line labeled gray line) and low single mutation fitness genes (solid line labeled red line) affect the percentage of the interactions covered, according to some examples of the present disclosure.
Figure 9:
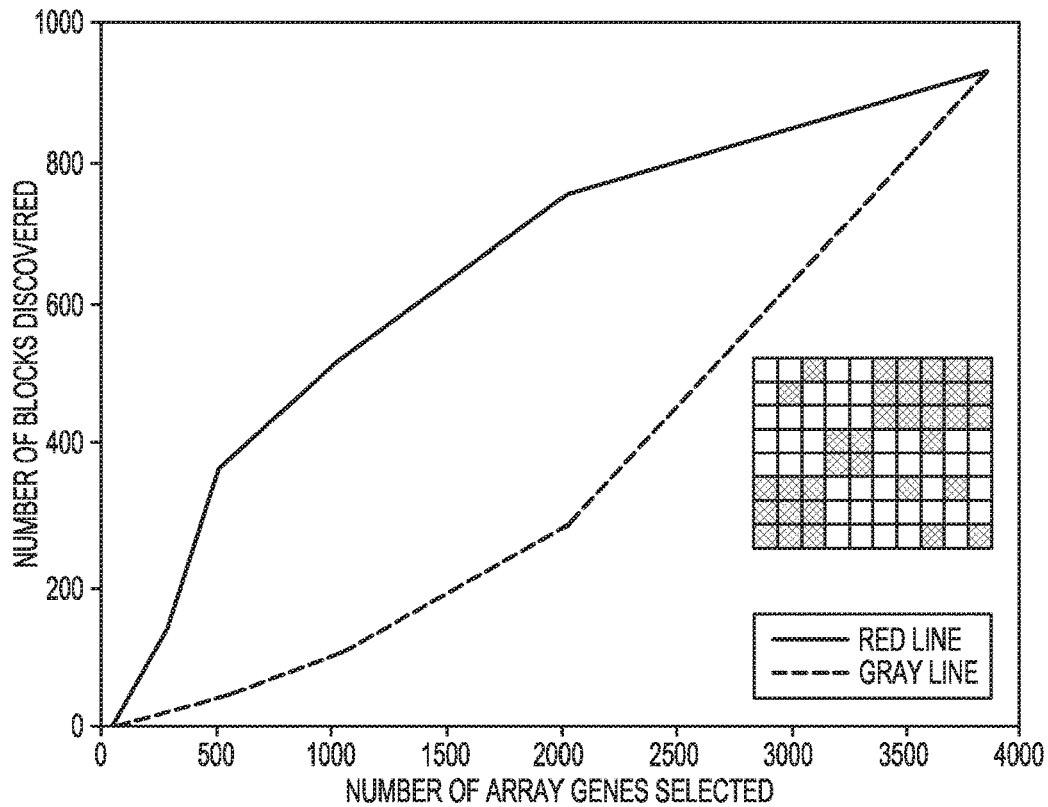
FIG. 9 is a chart showing how different selections of random genes dashed line labeled gray line) and low single mutation fitness genes (solid line labeled red line) affect the efficiency of detecting local structure in the genetic interaction network according to some examples of the present disclosure.

For the genetic interaction coverage and block structure use-cases, the performance scaled linearly with the number of random genes screened. This is shown in FIG. 8, which is a plot showing how different selections of random genes and low single mutation fitness genes from the array side of the genetic interactions representing almost the complete non-essential deletion collection affect the percentage of the interactions covered. Random genes are shown with the dashed line labeled gray line and low single mutation fitness genes are shown using the solid line labeled red line. This is also shown in FIG. 9, which is a plot of the number of bipartite or the block structure in the genetic interaction network. Random genes are shown with the dashed line labeled gray line and low single mutation fitness genes are shown using the solid line labeled red line. However, when genes with the lowest single mutant fitness were prioritized, a large fraction of the genetic interactions as well as the block structures were quickly recovered by screening only a small fraction of the genes. For example, around 60% of the interactions and around 70% of the block structure were covered by screening only 25% of the genome. The reason low single mutant fitness genes performed well may be because the hubs in the genetic interaction network are well-predicted by single mutant fitness, and therefore, prioritizing low single mutant fitness genes is a good proxy for prioritizing hubs.

In some examples, it was shown that screening against these diagnostic sets of genes works just as well as screening against a complete deletion collection for common genetic interaction use cases. In particular, if the objective is to discover functionally similar genes using genetic interactions or predict drug-targets using chemical and genetic interaction data, it has been shown that diagnostic set of genes is comparable, and sometimes better than even the complete deletion collection.

Example 1.2: Evaluation of the Compress-GI Algorithm

Figure 10:
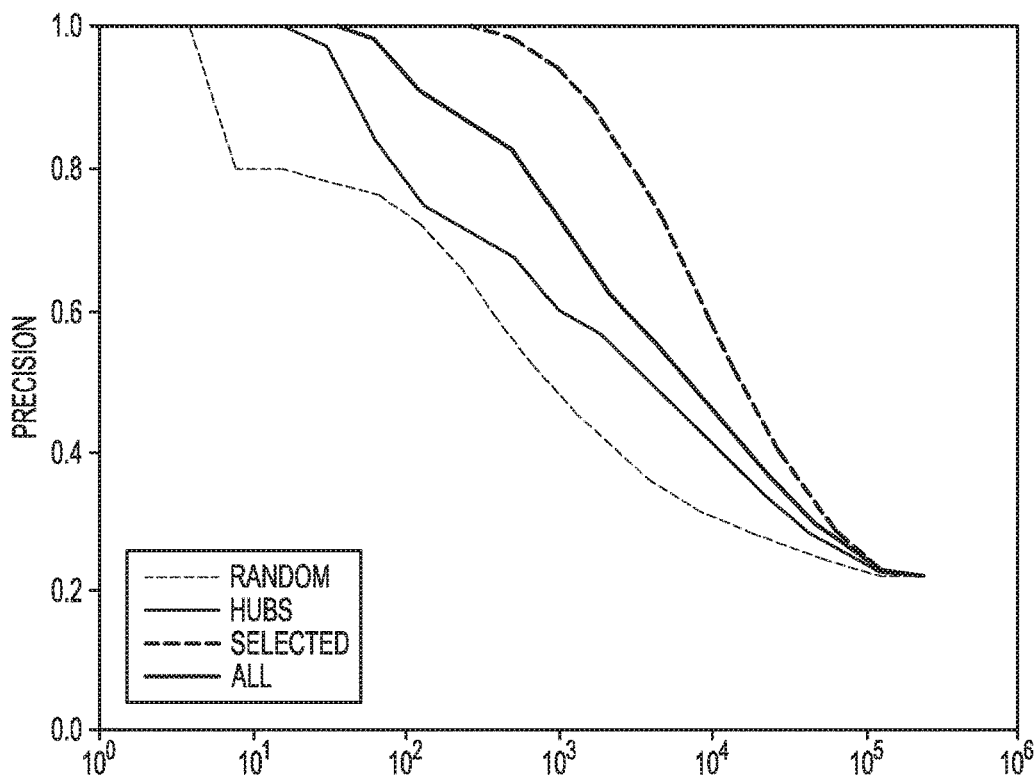
FIG. 10 is a chart showing a precision-recall evaluation of the selected genes and comparison with an equal number of random set of genes, equal number of hubs, and the entire genetic interaction dataset according to some examples of the present disclosure.
Figure 11:
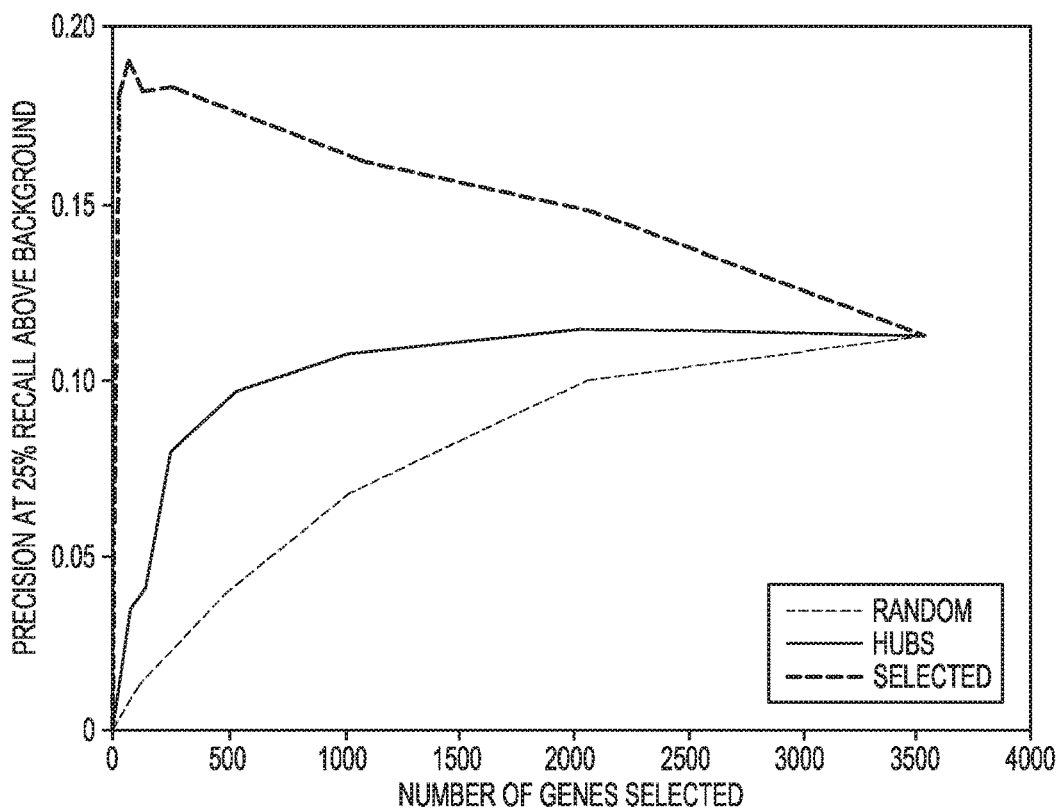
FIG. 11 is a chart showing the evaluation increasing numbers of selected genes according to some examples of the present disclosure.

The set of genes derived from the COMPRESS-GI algorithm provided a major improvement over a random screening strategy, both when evaluated globally on the complete Gene Ontology and for the functional category-specific evaluations. This is shown in FIGS. 10 and 11, which are plots showing precision-recall evaluation of the selected genes (dashed line labeled selected) and comparison with equal number of random set of genes (dashed line labeled random), an equal number of hubs (solid line labeled hubs), and the entire genetic interaction dataset (solid line labeled all).

Figure 12A:
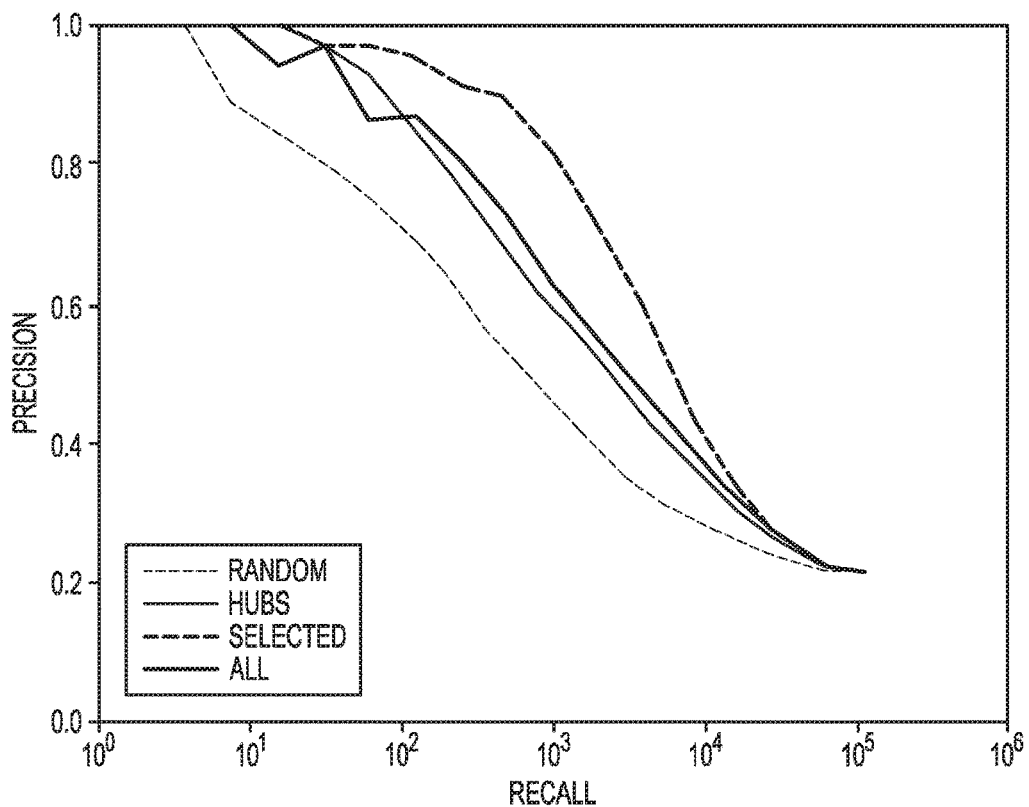
FIG. 12A shows a precision-recall performance evaluation of the COMPRESS-GI algorithm in a cross-validation setting where a fraction of the Gene Ontology was withheld during selection of the mutant strains according to some examples of the present disclosure.
Figure 12B:
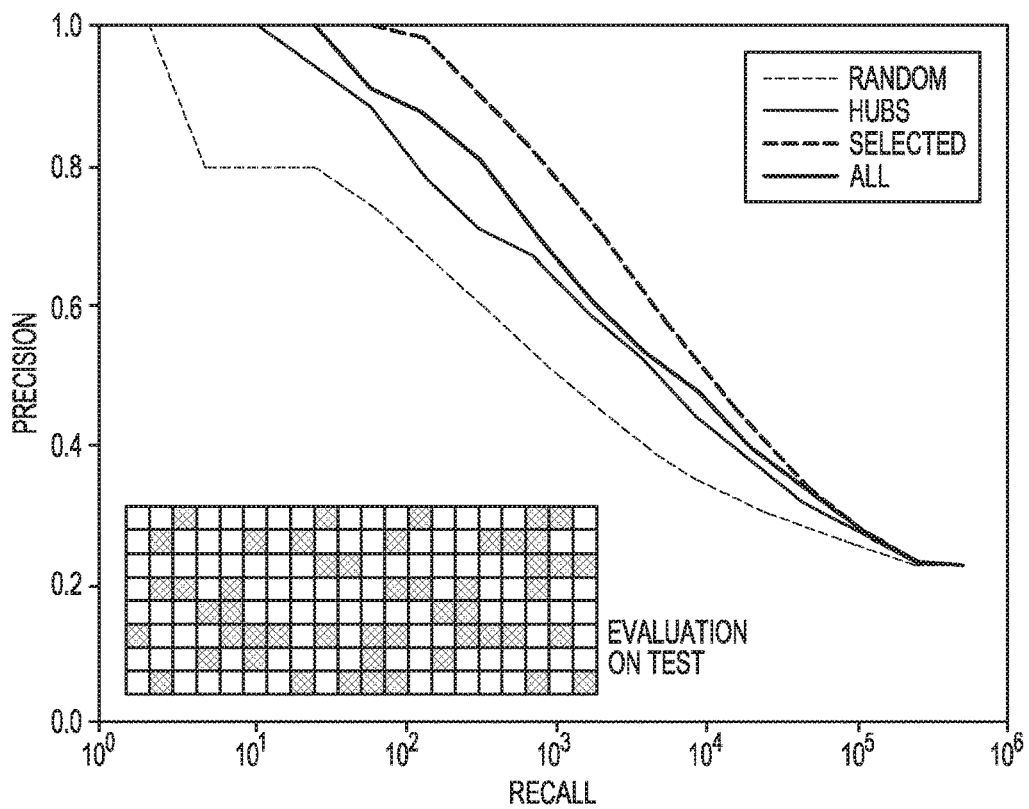
FIG. 12B shows a precision-recall performance evaluation of the COMPRESS-GI algorithm in a cross-validation setting where a fraction of the genetic interaction data was withheld during selection of the mutant strains according to some examples of the present disclosure.

The selected set of genes also performed better than an equal number of hubs, which may provide a reasonable strategy for maximizing the functional information derived from genetic interaction screens. The selected genes performed better than even the complete dataset for the global evaluation (FIG. 10), and comparably to the complete dataset on the function-specific evaluation (FIG. 11). It is noted that the precision-recall performance metric is not a monotonically increasing function with the number of genes selected. The better performance of the selected genes over the complete dataset suggests that there are non-informative or noisy genes in the complete dataset that actually detract from functional information in the genetic interaction data and thus, bring the precision-recall performance down relative to a smaller set of informative genes. To make sure that the algorithm was not simply overfitting, two cross-validation experiments were conducted. In the first cross-validation experiment, informative genes were identified by applying COMPRESS-GI on only 50% of the randomly selected genetic interaction query screens and then the ability of these selected genes was tested to provide profile information for the held out 50% of the genetic interactions screens. In the second experiment, 50% of the GO annotations were held out when selecting the informative gene set, and the selected set was tested for functional information on the held-out pairwise GO co-annotations. In both cross-validation experiments, the informative genes discovered in the training data were equivalently informative even for held-out data, suggesting that the approach is not overfitting. This is shown in FIGS. 12A and 12B which are precision-recall curves on training (FIG. 12A) and test GO standards (FIG. 12B), respectively. As shown in FIGS. 12A and 12B, the lines represent selected genes (dashed line labeled selected, a random set of genes (dashed line labeled random), hubs (solid line labeled hubs), and the entire genetic interaction dataset (solid line labeled all).

Since informative genes discovered from the array set can be prioritized for genetic interaction screening as query mutants, it was also checked whether informative array genes are also informative on the query side, and vice versa. To do this, only the square part of the *S. cerevisiae* genetic interaction data was considered (genes that appeared on both sets of the matrix) and informative sets of genes were discovered by running COMPRESS-GI on the array side and then the information content of the same set genes on the query side was checked, and vice versa. It is noted that the genes are informative in both cases, suggesting the method will indeed work for selecting new queries in practice.

Figure 13:
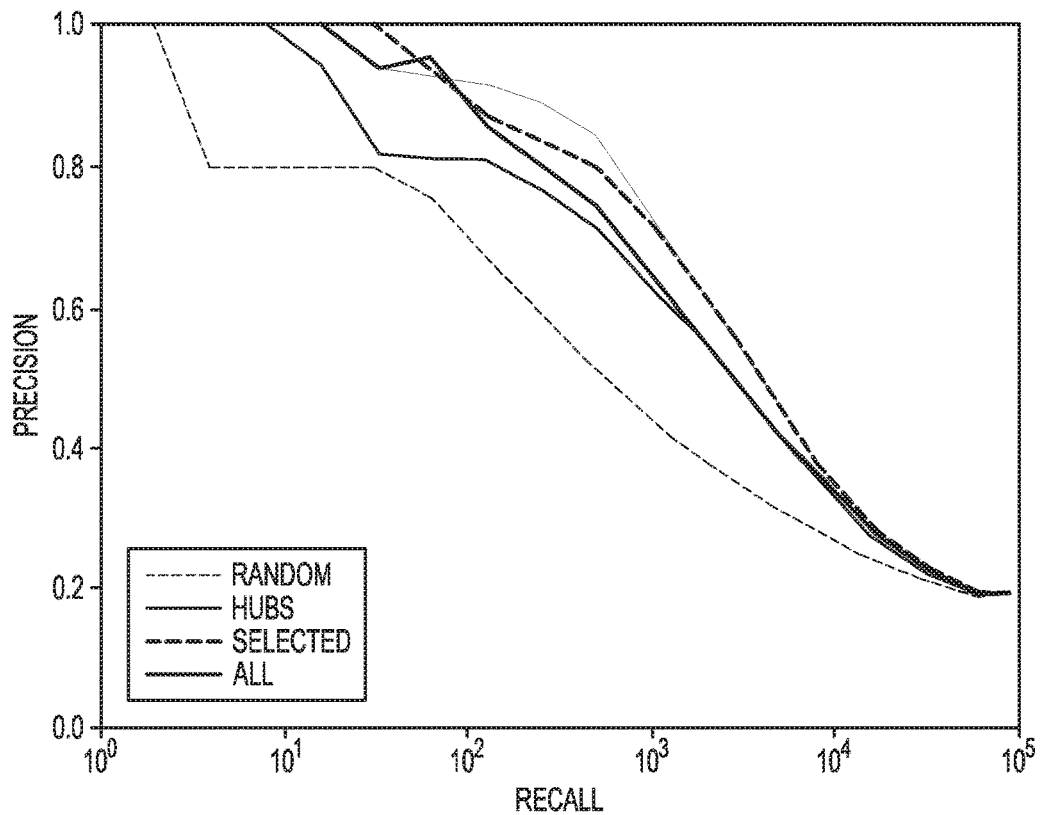
FIG. 13 is a chart showing the precision-recall curve for 100 genes selected by the COMPRESS-GI-LAF approach with iterative hub and random approaches according to some examples of the present disclosure.

Example 1.3: Iterative LAF: An Iterative Approach for Screening Genetic Interactions De-Novo The de novo genetic interaction screening scenario was simulated and evaluated on the Costanzo genetic interaction data. A submatrix of the genetic interaction matrix was selected such that genes on the array side are also on the query side which will ensure that screens for the genes which may be selected from the array side (1141 query genes by 1141 array genes). Ten genes were randomly screened first followed by 90 iteratively selected genes, for a total of 100 query gene screens. To measure the performance of each approach, a profile similarity network was constructed by measuring similarity between all pairs of array genes based on the 100 selected query genes, and evaluated with the Gene Ontology co-annotation standard using precision-recall analysis. Similar simulations were conducted to select 100 genes using the baseline iterative hubs approach. It was observed that the iterative LAF method performs better than both the iterative hubs approach and random screen selection. This is shown in FIG. 13, which is a plot comparing the precision-recall curves for 100 genes selected by this approach with iterative hub and random approaches. In FIG. 13, the lines represent selected genes (dashed line labeled selected, a random set of genes (dashed line labeled random), hubs (solid line labeled hubs), and the entire genetic interaction dataset (solid line labeled all).

Figure 14:
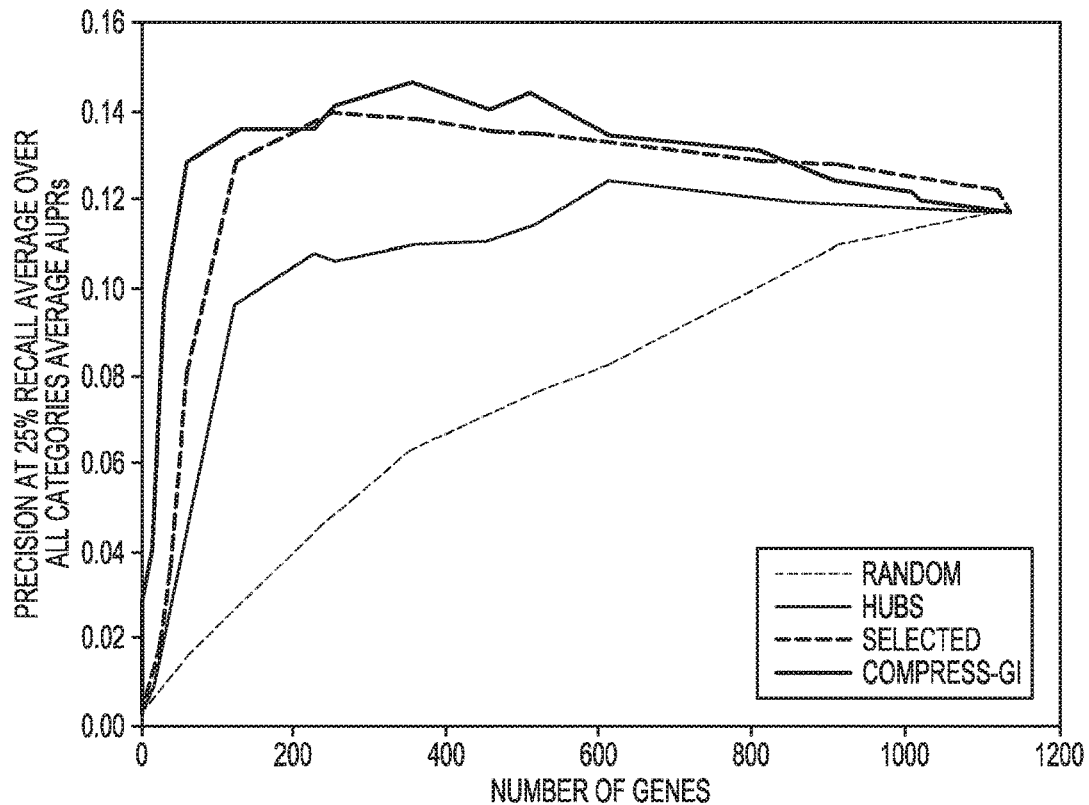
FIG. 14 is a chart showing a comparison of the precision at 25% recall performance of the different approaches as the number of genes selected is increased, according to some examples of the present disclosure.

For a broader perspective of how the algorithm performs as more genes are selected for screening, the selection was continued beyond 100 genes to the completion of the square matrix. The genes were then evaluated across different functional contexts using precision-recall statistics. Again, the precision at 25% recall performance averaged over the 13 functional contexts is higher for iterative LAF approach compared to iterative hubs and random. This is shown in FIG. 14, which is a plot showing the precision at 25% recall performance of the different approaches averaged across different functional categories. In FIG. 14, the lines represent selected genes (dashed line labeled selected, a random set of genes (dashed line labeled random), hubs (solid line labeled hubs), and the entire genetic interaction dataset (solid line labeled all).

To determine whether the method was generalizable to other species, a similar simulation approach was carried out on published *S. pombe* genetic interaction data. Similar to results in *S. cerevisiae* simulation, it was observed that the genes selected by the iterative LAF approach perform better than both random and iterative hub baseline approaches. The positive results in both species suggest that the algorithm will be useful in other organisms as well.

Figure 15:
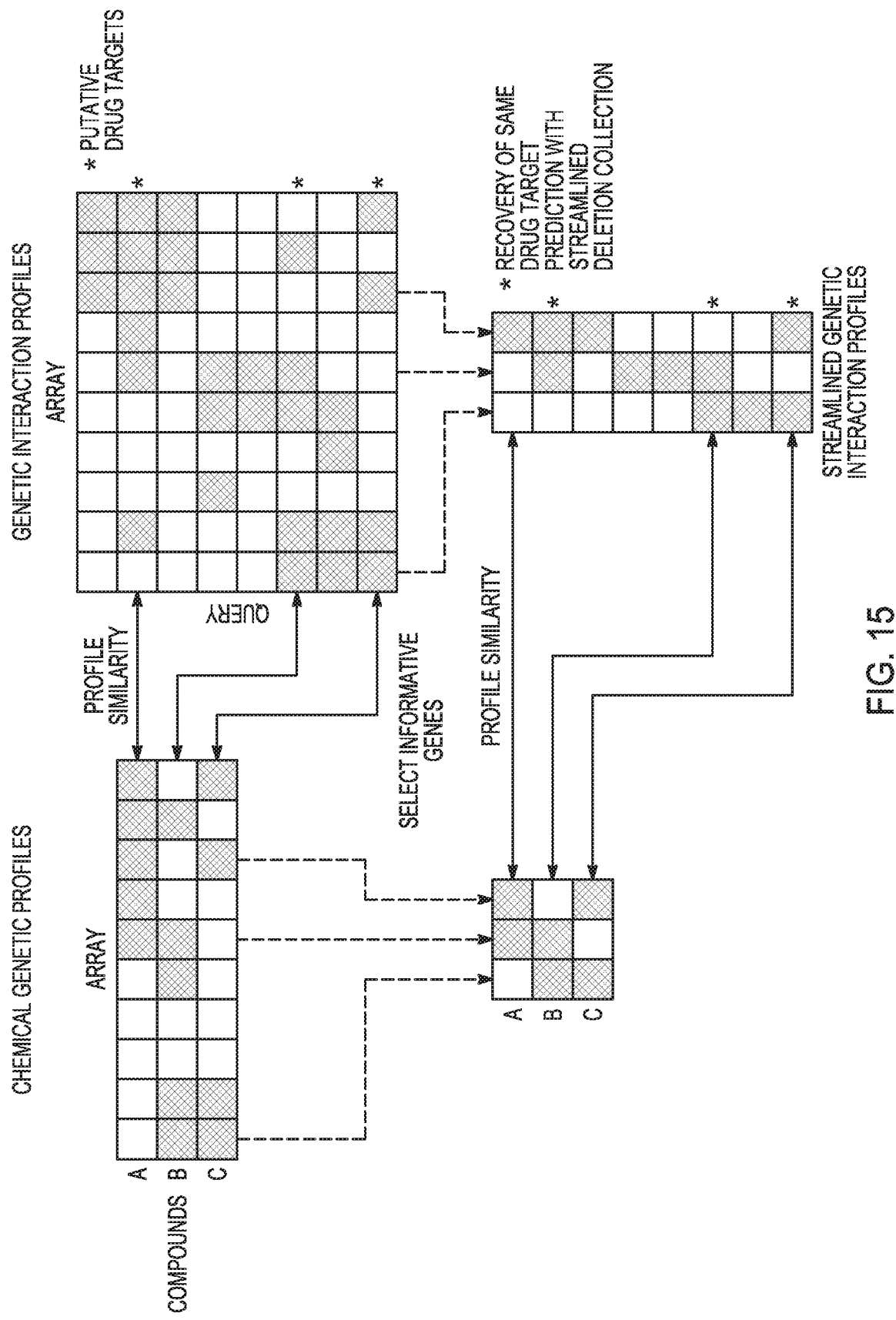
FIG. 15 is a schematic demonstrating that it is desirable to select genes such that even with partial profiles, the same drug-target predictions can be made according to some examples of the present disclosure.

Example 1.4: Application of Compress-GI to Optimize Large-Scale Chemical Genomic Screens The informative set of genes discovered by the COMPRESS-GI approach is directly applicable to the chemical genomics screening setting. This is shown in FIG. 15, which is schematic showing genes that are selected such that even with partial profiles, the same drug-target predictions can be made. In chemical genomics, mutant strains are treated by a compound to find the strains' resistance or sensitivity to the compound. This sensitivity profile can then be compared against other compounds to discover mechanistic similarities between the compounds or the sensitivity profile can be compared to a database of genetic interaction profiles to predict the target (protein) of the compound. A chemical genomic profile across the complete, whole genome collection of mutant strains would be desirable, but if the major aim of the experiment is to conduct profile correlation of the chemical profiles with other chemical or genetic profiles, then chemical genomics screens against an optimally selected set of genes discovered by COMPRESS-GI should perform as well as a whole genome screen. This optimization can save resources and make large-scale chemical genomics experiments feasible especially when amounts of compounds are a limiting constraint. The diagnostic set of genes selected roughly comprise 5% of the non-essential genome (200 genes), thus conducting chemical genomics experiments using this diagnostic set will reduce both the experimental cost and amount of compounds required by 20-fold.

To evaluate the set of genes selected by the COMPRESS-GI algorithm for the chemical genomics application, the drug-target prediction capability of the compound profile restricted was compared to selected genes with the compound profile restricted to an equal number of random genes. The drug-target prediction is conducted by finding a gene in genetic interaction data whose profile is most correlated with the compound's profile, and is based on the assumption that the compound's behavior will mimic the knock-out of the target gene. Using a yeast whole genome chemical genomics screening comprising 82 compounds, the correlation of the compound with its predicted target is higher for the partial profile consisting of selected genes compared to the correlation of the random partial profile of equal size (p-value <1.3*10-10). This observation suggests that the diagnostic set of genes outperforms an equal number of random genes. Further, when the enrichment of the top predicted targets is reviewed, the targets are more likely to be enriched for the selected partial profile compared to the random partial profile. This is shown in FIGS. 16 and 17.

Figure 16:
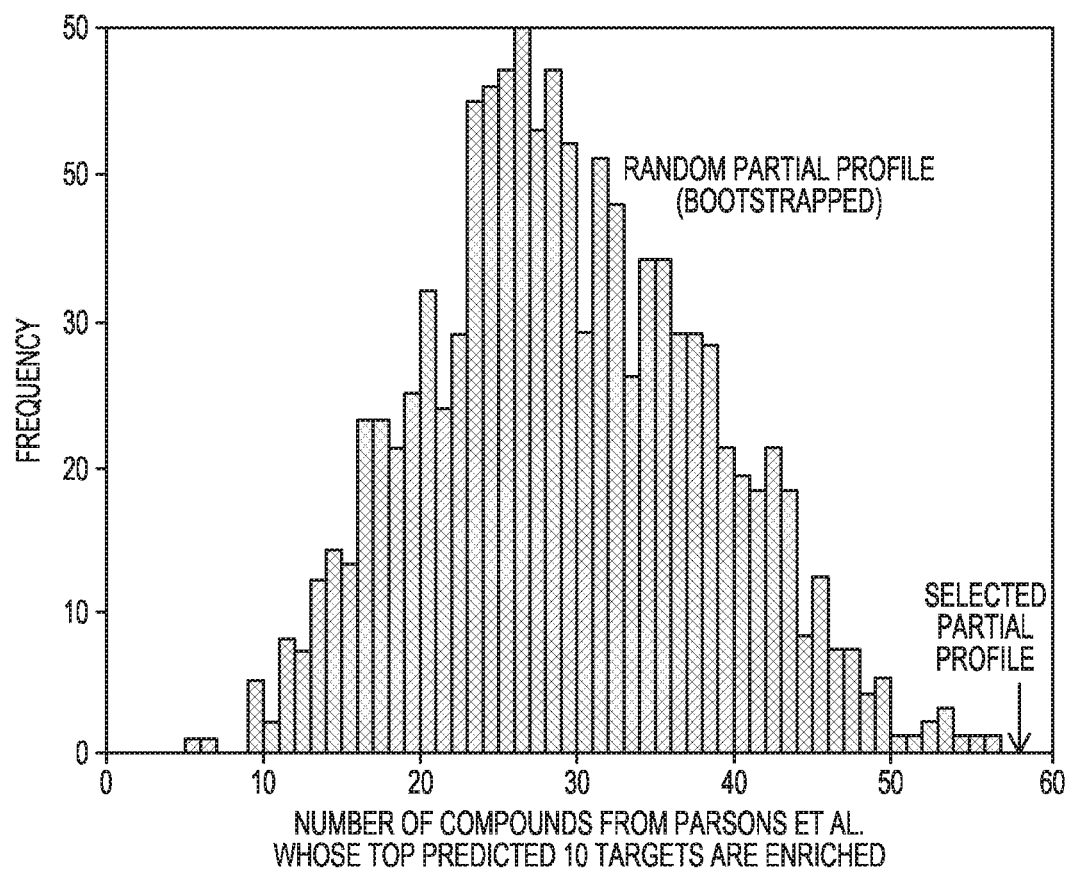
FIG. 16 is a chart showing a comparison of distributions of correlations of chemical compound's chemical genetic partial profile and its target's genetic interaction partial file based on the selected genes and random genes according to some examples of the present disclosure.
Figure 17:
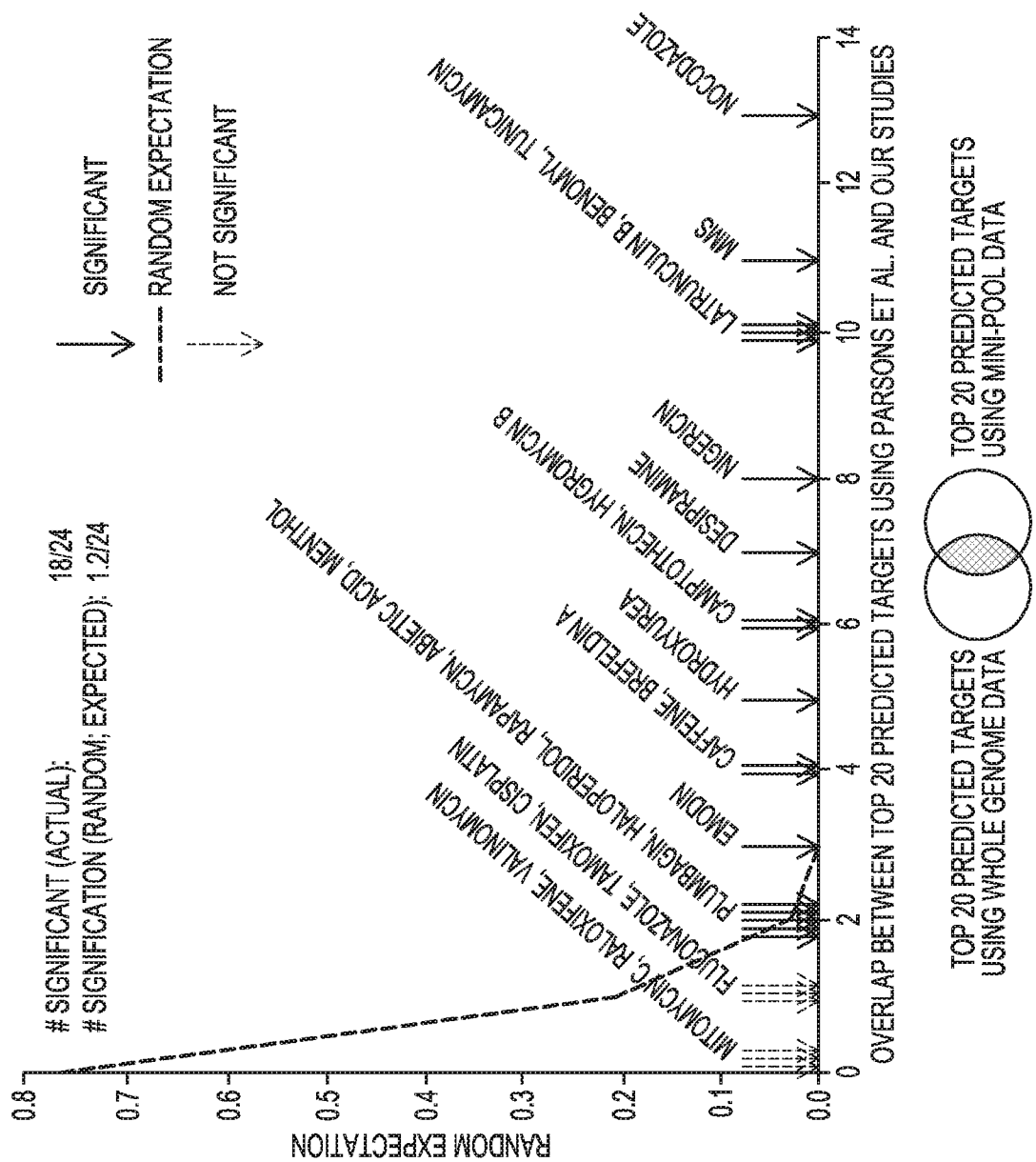
FIG. 17 is a chart showing a distribution of the number of compounds out of 82 compounds in a study whose targets based on the random partial profile targets are enriched according to some examples of the present disclosure.

FIG. 16 shows distributions of correlations of chemical compound's chemical genetic partial profile and its target's genetic interaction partial file based on the selected genes and random genes are compared. As shown 82 compounds are used for this validation. The target for each of the compounds is the query gene (row) in the genetic interaction data that has maximum correlation with the chemical compound's complete chemical genetic interaction profile. As shown in FIG. 17, the top 10 predicted targets for the compounds are checked for enrichment in Gene Ontology terms. FIG. 17 shows distribution of the number of compounds out of 82 compounds in Parsons whose targets based on the random partial profile targets are enriched. The randomization is conducted 100 times. The number of compounds whose targets are enriched with selected profile is shown with the arrow.

Significant enrichment of the top predicted targets give an indication that the target prediction based on the partial profile is not noisy and is focused on a particular functional neighborhood, which is most likely the actual target neighborhood. Based on this observation, it was determined that target prediction based on the diagnostic set of genes is less noisy compared to equal number of random genes. Moreover, the diagnostic set of genes performs (59 compounds show enrichment) better than even the entire profile (42 compounds show enrichment) for the enrichment of target prediction metric.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Embodiment 1 provides a method comprising:

selecting a first plurality of single gene mutants from a pool of possible single gene mutants of an organism wherein the first plurality of single gene mutants is less than a number of possible single mutants; and using a computer processor, iteratively selecting a second plurality of single gene mutants by selecting single gene mutants from the pool of possible single gene mutants that increases a sum of products of similarities between the first plurality of single gene mutants and corresponding functional relationships as indicated by co-annotations or other functional genomic data from the organism, wherein the second plurality of single gene mutants is larger in number than the first plurality of single gene mutants, and wherein the second plurality of single gene mutants is less than the number of possible single gene mutants of the organism; and outputting a set of genes comprising the first and second pluralities of single gene mutants.

Embodiment 2 provides the method of Embodiment 1, wherein increasing of the sum of products comprises determining a precision-recall value based on comparison to an external reference.

Embodiment 3 provides the method of Embodiment 2, wherein the process of iteratively selecting a second plurality of single gene mutants is terminated when the increase in the sum of products is substantially free of an increase in the precision-recall value.

Embodiment 4 provides the method of Embodiment 1, wherein a total number of the second plurality of the single gene mutants ranges from about 2 percent to about 40 percent of a total number of the possible single gene mutants of the organism.

Embodiment 5 provides the method of Embodiment 1, further comprising receiving a measurement of an interaction between a respective one of the first plurality of single gene mutants and a chemical.

Embodiment 6 provides the method of Embodiment 5, further comprising determining interactions between the second plurality of single gene mutants and the chemical.

Embodiment 7 provides a system comprising:

a memory:

a processor coupled to the memory, the memory including instructions, which when performed by the processor, cause the processor to perform the operations comprising:

iteratively selecting a second plurality of single gene mutants by selecting single gene mutants from a pool of possible single gene mutants that increases a sum of products of similarities between a first plurality of single gene mutants and functional relationships as indicated by co-annotations or other functional genomic data from an organism, wherein the second plurality of single gene mutants is larger in number than the first plurality of single gene mutants, and wherein the second plurality of single gene mutants is less than the number of possible single gene mutants of the organism; and outputting a set of genes comprising the first and second pluralities of single gene mutants.

Embodiment 8 provides the system of Embodiment 7, wherein increasing of the sum of products comprises determining a precision-recall value based on comparison to an external reference.

Embodiment 9 provides the system of Embodiment 8, wherein the process of iteratively selecting a second plurality of single gene mutants is terminated when the increase in sum of products is substantially free of an increase the precision-recall value.

Embodiment 10 provides the system of Embodiment 7, wherein a total number of the second plurality of the single gene mutants ranges from about 2 percent to about 40 percent of a total number of the possible single gene mutants of the organism.

Embodiment 11 provides the system of Embodiment 7, further comprising receiving a measurement of an interaction between a respective one of the first plurality of single gene mutants and a chemical.

Embodiment 12 provides the system of Embodiment 11, further comprising determining interactions between the second plurality of single gene mutants and the chemical.

Embodiment 13 provides a machine readable medium, including instructions, which when performed by a machine, causes the machine to perform the operations of:

iteratively selecting a second plurality of single gene mutants by selecting single gene mutants from a pool of possible single gene mutants that increases a sum of products of similarities between a first plurality of single gene mutants and functional relationships as indicated by co-annotations or other functional genomic data from an organism, wherein the second plurality of single gene mutants is larger in number than the first plurality of single gene mutants, and wherein the second plurality of single gene mutants is less than the number of possible single gene mutants of the organism; and outputting a set of genes comprising the first and second pluralities of single gene mutants.

Embodiment 14 provides the machine readable medium of Embodiment 13, wherein increasing of the sum of products comprises determining a precision-recall value based on comparison to an external reference.

Embodiment 15 provides the machine readable medium of Embodiment 14, wherein the process of iteratively selecting a second plurality of single gene mutants is terminated when the increase in the sum of products is substantially free of an increase the precision-recall value.

Embodiment 16 provides the machine readable medium of Embodiment 13, wherein a total number of the second plurality of the single gene mutants ranges from about 2 percent to about 40 percent of a total number of the possible single gene mutants of the organism.

Embodiment 17 provides the machine readable medium of Embodiment 13, further comprising receiving a measurement of an interaction between a respective one of the first plurality of single gene mutants and a chemical.

Embodiment 18 provides the machine readable medium of Embodiment 17, further comprising determining interactions between the second plurality of single gene mutants and the chemical.

Embodiment 19 provides the machine readable medium of Embodiment 18, wherein the chemical is a drug.

Embodiment 20 provides the machine readable medium of Embodiment 13, wherein the organism is a mammal.

What is claimed is:

1. A method comprising:
    using processor circuitry, receiving a selection of a first plurality of single gene mutants from a pool of possible single gene mutants of an organism wherein the first plurality of single gene mutants is less than a number of possible single mutants; and
    iteratively selecting a second plurality of single gene mutants from the pool of possible single gene mutants, wherein each of the selected second plurality of single gene mutants increases:
        a sum of products of similarities between the first plurality of single gene mutants and the second plurality of single gene mutants; and
        one or more corresponding functional relationships as indicated by co-annotations or other functional genomic data from the organism,
        wherein the second plurality of single gene mutants is larger in number than the first plurality of single gene mutants, and the second plurality of single gene mutants is less than a number of possible single gene mutants of the organism; and
    outputting a set of genes comprising the first plurality of single gene mutants and the second plurality of single gene mutants.

2. The method of claim 1, wherein increasing of the sum of products comprises determining a precision-recall value based on comparison to an external reference.

3. The method of claim 2, wherein the process of iteratively selecting a second plurality of single gene mutants is terminated when the increase in the sum of products is substantially free of an increase in the precision-recall value.

4. The method of claim 1, wherein a total number of the second plurality of the single gene mutants ranges from about 2 percent to about 40 percent of a total number of the possible single gene mutants of the organism.

5. The method of claim 1, further comprising receiving a measurement of an interaction between a respective one of the first plurality of single gene mutants and a chemical.

6. The method of claim 5, further comprising determining interactions between the second plurality of single gene mutants and the chemical.

7. The method of claim 1, further comprising selecting the first plurality of single gene mutants by using the processing circuitry.

8. The method of claim 1, wherein iteratively selecting the second plurality of single gene mutants further comprises ranking genes by score and choosing gene mutants based on ranking.

9. A system comprising:
    a memory;
    a processor coupled to the memory, the memory including instructions, which when performed by the processor, cause the processor to perform the operations comprising:
    receiving a selection of a first plurality of single gene mutants from a pool of possible single gene mutants of an organism wherein the first plurality of single gene mutants is less than a number of possible single mutants;
    iteratively selecting a second plurality of single gene mutants from a pool of possible single gene mutants, wherein each of the selected second plurality of single gene mutants increases a sum of products of similarities between the first plurality of single gene mutants and the second plurality of single gene mutants, and one or more corresponding functional relationships as indicated by co-annotations or other functional genomic data from an organism, wherein the second plurality of single gene mutants is larger in number than the first plurality of single gene mutants, and wherein the second plurality of single gene mutants is less than a number of possible single gene mutants of the organism; and outputting a set of genes comprising the first plurality of single gene mutants and second plurality of single gene mutants.

10. The system of claim 9, wherein increasing of the sum of products comprises determining a precision-recall value based on comparison to an external reference.

11. The system of claim 10, wherein the process of iteratively selecting a second plurality of single gene mutants is terminated when the increase in sum of products is substantially free of an increase the precision-recall value.

12. The system of claim 9, wherein a total number of the second plurality of the single gene mutants ranges from about 2 percent to about 40 percent of a total number of the possible single gene mutants of the organism.

13. The system of claim 9, further comprising receiving a measurement of an interaction between a respective one of the first plurality of single gene mutants and a chemical.

14. The system of claim 13, further comprising determining interactions between the second plurality of single gene mutants and the chemical.

15. A non-transitory machine readable medium, including instructions, which when performed by a machine, causes the machine to perform the operations of:

receiving a selection of a first plurality of single gene mutants from a pool of possible single gene mutants of an organism wherein the first plurality of single gene mutants is less than a number of possible single mutants;

iteratively selecting a second plurality of single gene mutants from a pool of possible single gene mutants, wherein each of the selected second plurality of single gene mutants increases a sum of products of similarities between the first plurality of single gene mutants and the second plurality of single gene mutants, and functional relationships as indicated by co-annotations or other functional genomic data from an organism, wherein the second plurality of single gene mutants is larger in number than the first plurality of single gene mutants, and wherein the second plurality of single gene mutants is less than the number of possible single gene mutants of the organism; and outputting a set of genes comprising the first plurality of gene mutants, and second plurality of single gene mutants.

16. The non-transitory machine readable medium of claim 15, wherein increasing of the sum of products comprises determining a precision-recall value based on comparison to an external reference.

17. The non-transitory machine readable medium of claim 16, wherein the process of iteratively selecting a second plurality of single gene mutants is terminated when the increase in the sum of products is substantially free of an increase the precision-recall value.

18. The non-transitory machine readable medium of claim 15, wherein a total number of the second plurality of the single gene mutants ranges from about 2 percent to about 40 percent of a total number of the possible single gene mutants of the organism.

19. The non-transitory machine readable medium of claim 15, further comprising receiving a measurement of an interaction between a respective one of the first plurality of single gene mutants and a chemical.

20. The non-transitory machine readable medium of claim 19, further comprising determining interactions between the second plurality of single gene mutants and the chemical.

21. The non-transitory machine readable medium of claim 20, wherein the chemical is a drug.

22. The non-transitory machine readable medium of claim 15, wherein the organism is a mammal.

* * * * *

UNITED STATES PATENT AND TRADEMARK OFFICE
CERTIFICATE OF CORRECTION

PATENT NO. : 11,017,880 B2
APPLICATION NO. : 15/475347
DATED : May 25, 2021
INVENTOR(S) : Deshpande et al.

It is certified that error appears in the above-identified patent and that said Letters Patent is hereby corrected as shown below:

On the Title Page

In Column 2, under "Other Publications", Line 10, before "screening", insert --genomics--

In the Drawings

Sheet 11 of 12, Fig. 16, On the left side (frequency), second one from the top delete "50" and insert --40-- therefor In the Specification In Column 1, Line 64, after "disclosure", insert --.--

In Column 5, Lines 29-30, delete "Positives." and insert --Positives,-- therefor In Column 5, Line 42, delete "is" and insert --1s-- therefor In Column 6, Line 32, delete "TP. FP" and insert --TP, FP-- therefor In Column 6, Line 46, delete "standard." and insert --standard,-- therefor In Column 7, Lines 2-3, delete "O(am²+m² log m)(a)(n)(f)(n)=O(m²n2(a+log m)af)." and insert --$O(am^2+m^2 \log m)(a)(n)(f)(n)=O(m^2n^2(a+\log m)af)$.-- therefor In Column 7, Line 8, delete "100.000th" and insert --100,000th-- therefor In Column 8, Line 25, delete "$(X^TG^TX)_{ii}$" and insert --$(X^TG^TX)_{ii}$,-- therefor In Column 8, Line 39, delete "m.n" and insert --m,n-- therefor Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,017,880 B2

In Column 8, Line 39, delete "10.000" and insert --10,000-- therefor

In Column 8, Line 40, delete "50.000" and insert --50,000-- therefor

In Column 8, Line 40, delete "450.000," and insert --450,000,-- therefor

In Column 8, Line 41, delete "350.000," and insert --350,000,-- therefor

In Column 8, Line 41, delete "200.000" and insert --200,000-- therefor

In Column 8, Line 42, delete "300.000)." and insert --300,000).-- therefor